US009039973B2

(12) United States Patent
Watson et al.

(10) Patent No.: US 9,039,973 B2
(45) Date of Patent: May 26, 2015

(54) HYBRID DIGITAL AND CHANNEL MICROFLUIDIC DEVICES AND METHODS OF USE THEREOF

(75) Inventors: Michael W. L. Watson, Toronto (CA); Mohamed Abdelgawad, Toronto (CA); Mais Jebrail, Richmond Hill (CA); Hao Yang, Toronto (CA); Aaron R. Wheeler, Toronto (CA)

(73) Assignee: THE GOVERNING COUNCIL OF THE UNIVERSITY OF TORONTO, Toronto, ON (CA)

( * ) Notice: Subject to any disclaimer, the term of this patent is extended or adjusted under 35 U.S.C. 154(b) by 1048 days.

(21) Appl. No.: 13/123,463

(22) PCT Filed: Oct. 13, 2009

(86) PCT No.: PCT/CA2009/001439
§ 371 (c)(1),
(2), (4) Date: Jul. 5, 2011

(87) PCT Pub. No.: WO2010/040227
PCT Pub. Date: Apr. 15, 2010

(65) Prior Publication Data
US 2012/0083046 A1    Apr. 5, 2012

Related U.S. Application Data

(60) Provisional application No. 61/136,896, filed on Oct. 10, 2008.

(51) Int. Cl.
*B01L 99/00* (2010.01)
*G01N 1/28* (2006.01)
(Continued)

(52) U.S. Cl.
CPC ....... *G01N 27/44791* (2013.01); *H01J 49/0445* (2013.01); *H01J 49/167* (2013.01);
(Continued)

(58) Field of Classification Search
CPC .............. G01N 35/10; G01N 35/1095; G01N 2035/10; G01N 2035/1041; G01N 27/44791; H01J 49/04; H01J 49/0445; H01J 49/165; H01J 49/167; B01L 3/502715; B01L 3/502792; B01L 3/502753; B01L 2200/027; B01L 2300/0816; B01L 2300/089; B01L 2400/0415; B01L 2400/0421
See application file for complete search history.

(56) References Cited

U.S. PATENT DOCUMENTS

| 4,569,575 A | 2/1986 | Le Pesant et al. |
| 4,636,785 A | 1/1987 | Le Pesant |

(Continued)

FOREIGN PATENT DOCUMENTS

| CA | 2470847 | 7/2003 |
| WO | 03045556 A2 | 6/2003 |

(Continued)

OTHER PUBLICATIONS

Kim, Woong et al. Anal. Chem. (2007) 79 3703-3707.*
(Continued)

*Primary Examiner* — Christopher A Hixson
(74) *Attorney, Agent, or Firm* — Lynn C. Schumacher; Hill & Schumacher; Stephen W. Leonard

(57) ABSTRACT

The present invention provides a hybrid digital and channel microfluidic device in the form of an integrated structure in which a droplet may be transported by a digital microfluidic array and transferred to a microfluidic channel. In one aspect of the invention, a hybrid device comprises a first substrate having a digital microfluidic array capable of transporting a droplet to a transfer location, and a second substrate having a microfluidic channel. The first and second substrates are affixed to form a hybrid device in which an opening in the microfluidic channel is positioned adjacent to the transfer location, so that a droplet transported to the transfer location contacts the channel opening and may enter the channel. The invention also provides methods of performing separations using a hybrid digital and channel microfluidic device and methods of assembling a hybrid digital microfluidic device.

25 Claims, 17 Drawing Sheets

(51) Int. Cl.

| | |
|---|---|
| *G01N 27/62* | (2006.01) |
| *B05B 5/025* | (2006.01) |
| *B23P 19/00* | (2006.01) |
| *G01N 27/447* | (2006.01) |
| *G01N 35/10* | (2006.01) |
| *B01L 3/00* | (2006.01) |
| *H01J 49/04* | (2006.01) |
| *H01J 49/16* | (2006.01) |

(52) U.S. Cl.
CPC ....... *G01N 35/10* (2013.01); *G01N 2035/1041* (2013.01); *G01N 35/1095* (2013.01); *H01J 49/04* (2013.01); *H01J 49/165* (2013.01); *B01L 3/502715* (2013.01); *B01L 3/502753* (2013.01); *B01L 3/502792* (2013.01); *B01L 2200/027* (2013.01); *B01L 2300/0816* (2013.01); *B01L 2300/089* (2013.01); *B01L 2400/0415* (2013.01); *B01L 2400/0421* (2013.01)

(56) References Cited

U.S. PATENT DOCUMENTS

| | | | |
|---|---|---|---|
| 4,818,052 | A | 4/1989 | Le Pesant et al. |
| 5,486,337 | A | 1/1996 | Ohkawa |
| 6,007,690 | A * | 12/1999 | Nelson et al. ............... 204/601 |
| 6,352,838 | B1 | 3/2002 | Krulevitch et al. |
| 6,565,727 | B1 * | 5/2003 | Shenderov ............... 204/600 |
| 6,596,988 | B2 | 7/2003 | Corso et al. |
| 6,723,985 | B2 | 4/2004 | Schultz et al. |
| 6,773,566 | B2 | 8/2004 | Shenderov |
| 6,911,132 | B2 | 6/2005 | Pamula et al. |
| 6,989,234 | B2 | 1/2006 | Kolar et al. |
| 7,147,763 | B2 | 12/2006 | Elrod et al. |
| 7,163,612 | B2 | 1/2007 | Sterling et al. |
| 7,214,302 | B1 | 5/2007 | Reihs et al. |
| 7,255,780 | B2 | 8/2007 | Shendervo |
| 7,328,979 | B2 | 2/2008 | Decre et al. |
| 7,329,545 | B2 | 2/2008 | Pamula et al. |
| 7,391,020 | B2 | 6/2008 | Bousse et al. |
| 2002/0043463 | A1 | 4/2002 | Shenderov |
| 2004/0058450 | A1 | 3/2004 | Pamula et al. |
| 2004/0171169 | A1 | 9/2004 | Kallury et al. |
| 2004/0211659 | A1 | 10/2004 | Velev |
| 2005/0115836 | A1 | 6/2005 | Reihs |
| 2005/0133370 | A1 * | 6/2005 | Park et al. ............... 204/450 |
| 2005/0148091 | A1 | 7/2005 | Kitaguchi et al. |
| 2005/0191759 | A1 | 9/2005 | Pedersen-Bjergaard et al. |
| 2007/0095407 | A1 | 5/2007 | Chen et al. |
| 2007/0148763 | A1 | 6/2007 | Huh et al. |
| 2007/0242111 | A1 | 10/2007 | Pamula et al. |
| 2008/0044814 | A1 | 2/2008 | Ren et al. |
| 2008/0050834 | A1 | 2/2008 | Pamula et al. |
| 2008/0131904 | A1 | 6/2008 | Parce et al. |
| 2008/0156983 | A1 | 7/2008 | Fourrier et al. |
| 2008/0185339 | A1 | 8/2008 | Delapierre et al. |
| 2008/0210558 | A1 | 9/2008 | Sauter-Starace et al. |
| 2008/0281471 | A1 | 11/2008 | Smith et al. |
| 2009/0203063 | A1 | 8/2009 | Wheeler et al. |
| 2010/0081578 | A1 | 4/2010 | Wheeler et al. |
| 2010/0087633 | A1 | 4/2010 | Wheeler et al. |
| 2010/0213074 | A1 | 8/2010 | Mousa et al. |
| 2010/0311599 | A1 | 12/2010 | Wheeler et al. |
| 2011/0107822 | A1 * | 5/2011 | Bunner et al. ............... 73/61.52 |

FOREIGN PATENT DOCUMENTS

| | | |
|---|---|---|
| WO | 2005068993 | 7/2005 |
| WO | 2005118129 A1 | 12/2005 |
| WO | 2007120241 A2 | 10/2007 |
| WO | 2007136386 A1 | 11/2007 |
| WO | 2008051310 A3 | 5/2008 |
| WO | 2009111723 A1 | 9/2009 |
| WO | 2009111723 A9 | 9/2009 |
| WO | 2009/111431 | 9/2011 |

OTHER PUBLICATIONS

Shih-Kang Fan. "Cross-scale electric manipulations of cells and droplets by frequency-modulated dielectrophoresis and electrowetting" The Royal Society of Chemistry (2008), Lab Chip vol. 8, pp. 1325-1331.

Ting-Hsuan Chen. "Selective Wettability Assisted Nanoliter Sample Generation Via Electrowetting-Based Transportation," Proceedings of the Fifth International Conference on Nanochannels, Microchannels and Minichannels (ICNMM) (Jun. 18-20, 2007).

Horigmel Yu. "A plate reader-compatible microcharznel array for cell biology assays," The Royal Society of Chemistry (2007) Lab Chip vol. 7, pp. 388-391.

Marc A. Unger. "Monolithic Microfabricated Valves and Pumps by Multilayer Soft Lithography," Science (2000) vol. 288.

A.S. Verkman, "Drug Discovery in Academia," Am J Physiol Cell Physiol (2004) vol. 286. pages 465-474. El.

Jamil El-Ali. "Cells on chips," Nature (2006) Insight Review, vol. 442.

Darren R. Link. "Electric Control of Droplets in Microfluidic Devices." Communications, Angew Chem. Int (2006) vol. 45 pp. 2556-2560.

Wheeler Aaron A. "Electrowetting-Based Microfluidics for Analysis of Peptides and Proteins by Matrix-Assisted Laser Desorption/Ionization Mass Spectrometry," (Aug. 2004) Anal Chem. vol. 76, No. 16.

Eun Zoo Lee, "Removal of bovine serum albumin using solid-phase extraction with in-situ polymerized stationary phase in a microfluidic device," ScienceDirect, Journal of Chromatography A. (2008) vol. 1187, pp. 11-17.

Hsih Yin Tan. "A lab-on-a-chip for detection of nerve agent sarin in blood." The Royal Society of Chemistry (2008), Lab Chip vol. 8, pp. 885-891.

Kai-Cheng Chuang. "Direct Handwriting Manipulation of Droplets by Self-Aligned Mirror-EWOD Across a Dielectric Sheet," MEMS (Jan. 2006) pp. 22-26.

Mohamed Abdelgawad. "Low-cost, rapid-prototyping of digital microfluidics devices," Springer, Microfluid Nanofluid (2008) vol. 4, pp. 349-355.

Eric Lebrasseur. "Two-dimensional electrostatic actuation of droplets using a single electrode panel and development of disposable plastic film card," ScienceDirect, Sensors and Actuators (2007) vol. 136, pp. 359-366.

Mais J. Jebrail. "Digital Microfluidic Method for Protein Extraction by Precipitation," Anal. Chem. (2009) vol. 81, No. 1.

Debalina Chatterjee. "Droplet-based microfluidics with nonaqueous solvents and solutions," The Royal Society of Chemistry (2006), Lab Chip vol. 6, pp. 199-206.

Hyelin Moon. An integrated digital mic:rofluidic chip for multiplexed proteomic sample preparation and analysis by MALDI-MS, The Royal Society of Chemistry (2006), Lab Chip vol. 6, pp. 1213-1219.

Chao Yung Fan et al: Electrically 1-23 INV. Programmable Surfaces for Configurable Patterning of Cells, Advanced Materials, vol. 20, No. 8, Apr. 21, 2008 , pp. 1418-1423.

Abdelgawad et al. "Hybrid microfluidics: A digital-to-channel interface for in-line sample processing and chemical separations." Lab on a Chip. vol. 9. No. 8. pp. 1046-1051. Feb. 18, 2009.

* cited by examiner

HYBRID DIGITAL AND CHANNEL MICROFLUIDIC DEVICES AND METHODS OF USE THEREOF

CROSS-REFERENCE TO RELATED APPLICATION

This application is a National Phase application claiming the benefit of PCT/CA2009/001439 filed on Oct. 13, 2009, entitled "HYBRID DIGITAL AND CHANNEL MICROFLUIDIC DEVICES AND METHODS OF USE THEREOF", which was filed in English; which further claims priority to U.S. Provisional Application No. 61/136,896, filed on Oct. 10, 2008, the entire contents of which are incorporated herein by reference.

FIELD OF THE INVENTION

This invention relates to the integration of digital and channel microfluidic devices. More particularly, the invention relates to methods of separation using hybrid digital microfluidic and channel microfluidic devices.

BACKGROUND OF THE INVENTION

Microfluidic devices have revolutionized analytical separations, facilitating fast analyses with higher resolution, higher efficiency, and lower reagent consumption relative to their macro-scale counterparts [1]. Microchannel-based devices have been used to separate mixtures of analytes ranging from small molecules like amino acids and neurotransmitters to large molecules like DNA and proteins [2]. To complement chemical separations, microchannel-based systems have been developed incorporating pre-column reactions, including enzymatic digestion [3], organic synthesis [4], and fluorescent derivatization [5,6]. These techniques represent the promise of microfluidics for forming fully integrated lab-on-a-chip devices.

Unfortunately, the number and scope of lab-on-a-chip devices capable of integrating pre-column reactions with separations is limited. For example, there are no microfluidic methods reported that are adaptable to shotgun proteomics [7], in which samples are subjected to a rigorous, multi-step processing regimen requiring several days to complete [8]. This deficit is largely mechanistic—managing multiple reagents with precise control over position and reaction time in microchannels is complicated by the near-universal effects of hydrostatic and capillary flows [9-11]. The development of integrated microvalves [12] offers some relief from this problem; however, the complicated fabrication and control infrastructure required for this technology has limited its widespread use [13]. Another technique that might be useful for pre-column reactions and separations is multi-phase microfluidic systems (i.e., droplets in channels) [14]. In recent work, Edgar et al. [15] and Roman et al. [16] reported methods capable of delivering droplets from such systems directly into separation channels. This is an exciting new development, but the droplets-in-channels paradigm is not ideally suited for controlling chemical reactions, as droplets (regardless of their contents) are controlled in series.

An alternative miniaturized fluid handling format to microchannels is digital microfluidics (DMF), a technique in which discrete fluidic droplets are manipulated by electrostatic forces on an array of electrodes coated with an insulating dielectric [17-19]. DMF is well-suited for carrying out sequential chemical reactions in which droplets containing different reagents [20,21] and phases [22] can be dispensed from reservoirs, moved, merged, mixed and split [23]. For example, it was recently shown that a multistep proteomic sample processing workup can be achieved by digital microfluidics, in which protein samples were sequentially reduced, alkylated, and digested [24]. Likewise, a DMF method to purify proteins from serum in a multistep process comprising precipitation, rinsing, and resolubilization has also been implemented [25]. These types of sequential processing regimens are difficult to implement using microchannels.

Unfortunately, prior art adaptations of digital microfluidic technology to separation and other analytical methods have focused on the use of capillaries. Capillaries are broadly known in the art as being distinct from microchannel devices. Specifically, capillaries are tubular structures having an inner and outer diameter in which the inner diameter is sufficiently small to promote the flow of liquid by capillary action.

One example of a DMF-capillary device is postulated by Fair [26], wherein there is a description of a platform involving the transfer of sample from an electrowetting-on-dielectric device to a capillary electrophoresis device that includes a capillary for separation. This scheme includes two separate devices, namely a DMF array for sample pre-processing and a capillary device for separation. The use of two separate devices leads to a host of technical difficulties not addressed in [26], including the precise spatial alignment required to achieve flow from one device to another, and difficulty in adapting and securing capillaries for use with a DMF elements.

Another capillary-DMF device is provided in International Patent Application WO/2009/111431, which provides a DMF array that is connected to a capillary for transferring liquid to another physically separate analysis device. In specific embodiments, the DMF device is adapted to an electrospray ionization compatible tip to allow interfacing with a mass spectrometer. Unfortunately, such a device presents numerous practical challenges including the integration of a tubular capillary with a planar DMF device. Further, the spatial extension of the capillary beyond the planar DMF substrate presents a very high risk of breakage. This high risk of breakage is further exacerbated by designs in which a capillary is suspended below the DMF substrate, which would almost certainly lead to breakage during routine use.

An improved device adapting electrowetting technology to microchannels is provided by International Patent Application No. WO 2007/048111, which discloses a microfluidic channel that incorporates electrowetting for the extraction of separated species. The device includes a microfluidic channel, with electrodes located at either end of the channel that draw in sample for electrophoretic separation. In addition, the microfluidic channel includes a wall opening located along the channel, where electrowetting is employed to extract a target separated along the channel. The wall opening can be provided anywhere along a non-walled liquid column or at any wall opening in between the ends of a wall-bounded liquid channel. While extracting a droplet from one side of the channel, a second refill droplet is added on the other side of the channel to prevent remixing of separated species.

Although this device succeeds in providing droplet-based extraction, it suffers from a number of disadvantages that limit its practical use as a microfluidic separation device. First, extracting droplets from a channel used for a chemical separation will destroy the resolution gained in the separation as the separated components will recombine as the droplets are sampled off the channel. Second, and most notably, all initial sample processing must be performed off-line, using either manual methods or another automated system.

Accordingly, it would therefore be advantageous to provide an improved microfluidic device that provides the capability of both sample pre-processing and microfluidic separation without suffering from the problems associated with aligning multiple devices and without requiring the use of tubular capillaries for separation.

SUMMARY OF THE INVENTION

The present invention solves the aforementioned problems associated with prior art microfluidic devices by providing a hybrid digital and channel microfluidic device, in concert with methods of using such hybrid device for chemical separation and other analytic and pre-analytic processes. Unlike prior art designs and methods, the present invention uniquely comprises a single, hybrid device and integrates a digital microfluidic array with microfluidic channels.

In a first aspect of the invention, there is provided a hybrid microfluidic device comprising:

a first substrate having an upper surface comprising a digital microfluidic array, wherein the array is adapted to transport a fluidic droplet to a transfer location on the first substrate;

a second substrate comprising a microfluidic channel, wherein an opening of the microfluidic channel is formed in a surface of the second substrate, and wherein the opening of the microfluidic channel is positioned adjacent to the transfer location, and wherein a droplet positioned at the transfer location is contacted with the opening; and wherein at least a portion of the droplet may be transferred from the transfer location into the channel by a fluidic interfacing means.

In another embodiment of the invention, a method of performing separations using a hybrid digital and channel microfluidic device is provided. Unlike prior art methods, the channel microfluidic network is pre-loaded with a buffer or separation medium, and the hybrid digital and channel device is subsequently employed to perform a separation on a droplet of sample.

Accordingly, in another aspect of the invention, there is provided a method of separating a target material using a hybrid digital and channel microfluidic device, the device comprising a digital microfluidic array interfaced with a microfluidic channel network, the method comprising the steps of:

a) providing a quantity of separation liquid to the device at a location addressable by the array;

b) actuating the array to transport a droplet of the separation liquid into contact with an opening of the microfluidic channel network; wherein the droplet of the separation liquid enters the microfluidic channel network via capillary force;

c) repeating step (b) until the channel contains a sufficient quantity of the separation liquid;

d) providing a quantity of sample to the device at a location addressable by the array;

e) actuating the array to transport a droplet of the sample into contact with the opening of the microfluidic channel network; wherein at least a portion of the droplet of the sample enters the microfluidic channel network via a fluidic interfacing means; and f) separating the target material within the microfluidic channel network using a separation means, wherein the microfluidic channel network comprises one or more microfluidic channels.

In yet another aspect of the invention, there is provided a method of pre-analytic preparation of a hybrid digital and channel microfluidic device, the device comprising a digital microfluidic array interfaced with a microfluidic channel network, the method comprising the steps of:

a) providing a quantity of separation liquid to the device at a location addressable by the array;

b) actuating the array to transport a droplet of the separation liquid into contact with an opening of the microfluidic channel network; wherein the a droplet of the separation liquid enters the microfluidic channel network via a capillary force;

c) repeating step (b) until the channel contains a sufficient quantity of the separation liquid;

d) providing a quantity of sample to the device at an additional location addressable by the array; and e) actuating the array to transport a droplet of the sample into contact with the opening of the microfluidic channel network; wherein at least a portion of the droplet of the sample enters the microfluidic channel network via a fluidic interfacing means;

wherein the microfluidic channel network comprises one or more microfluidic channels.

In yet another embodiment of the invention, there is provided a method of assembling a hybrid digital and channel microfluidic device, the device comprising a first substrate having an upper surface comprising an array of electrodes and a second substrate comprising a microfluidic channel, wherein an opening of the microfluidic channel is formed in a surface of the second substrate, the method comprising the steps of:

affixing a portion of the second substrate to a portion of the first substrate to form a single structure, wherein the opening of the microfluidic channel is positioned adjacent to an electrode in the array of electrodes;

blocking one or more openings of the microfluidic channel with a blocking means;

providing one or more insulating layers to the array of electrodes; and removing the blocking means.

A further understanding of the functional and advantageous aspects of the invention can be realized by reference to the following detailed description and drawings.

BRIEF DESCRIPTION OF THE DRAWINGS

The embodiments of the present invention are described with reference to the attached figures, wherein.

DETAILED DESCRIPTION OF THE INVENTION

Generally speaking, the systems described herein are directed to hybrid digital and channel microfluidic devices. As required, embodiments of the present invention are disclosed herein. However, the disclosed embodiments are merely exemplary, and it should be understood that the invention may be embodied in many various and alternative forms. The figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to hybrid digital and channel microfluidic devices.

As used herein, the term "microfluidic channel" refers to a confined channel provided within or on a substrate, where at least one cross-sectional dimension of the channel is from about 0.1 micrometers to about 1 mm.

As used herein, the term "capillary action" refers to the flow of a liquid though a geometrically confined or porous material due to surface interaction forces. The term "capillary action" as used herein does not imply the presence of a capillary tube.

As used herein, the term "sample" is used in its broadest sense. In one sense, it may include clinical samples, isolated nucleic acids, or isolated microorganisms. In preferred embodiments, a sample is obtained from a biological source (i.e., a "biological sample"), such as tissue, bodily fluid, or microorganisms collected from a subject. Sample sources include, but are not limited to, mucus, sputum (processed or unprocessed), bronchial alveolar lavage (BAL), bronchial wash (BW), blood, bodily fluids, cerebrospinal fluid (CSF), urine, plasma, serum, or tissue (e.g., biopsy material). Samples may also be obtained from environmental or industrial sources. Samples may be directly provided or may be pre-processed, for example, by filtering, lysing, purification, or modified by the addition of a reagent or buffer.

Hybrid Lateral Digital and Channel Microfluidic Device Overview

Figure 1:
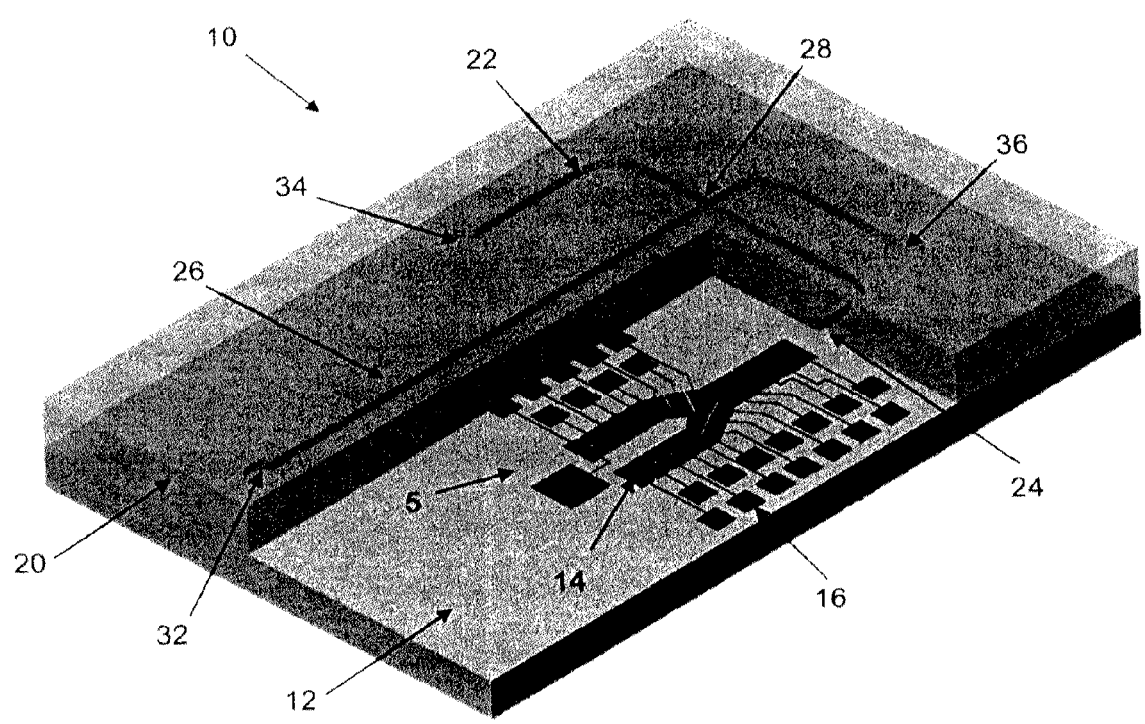
FIG. 1 shows a hybrid digital and channel microfluidic device.

FIG. 1 illustrates a preferred embodiment of the invention in which a hybrid digital and channel microfluidic device is shown generally at 10. The device includes a first substrate 12 having thereon a digital microfluidic array 5 comprising electrodes 14 electrically connected to contact pads 16. Attached to a surface of first substrate 12 is a second substrate 20 having a microfluidic channel 22 formed therein. Microfluidic channel 22 forms an opening 24 in second substrate 20. Second substrate further optionally includes a second microfluidic channel 26 intersecting first microfluidic channel 22 at intersection point 28. Access ports 32, 34 and 36 are provided in second substrate 20, and extend from a bottom surface to a top surface of second substrate 20, thereby providing external access to channels 22 and 26.

Figure 2:
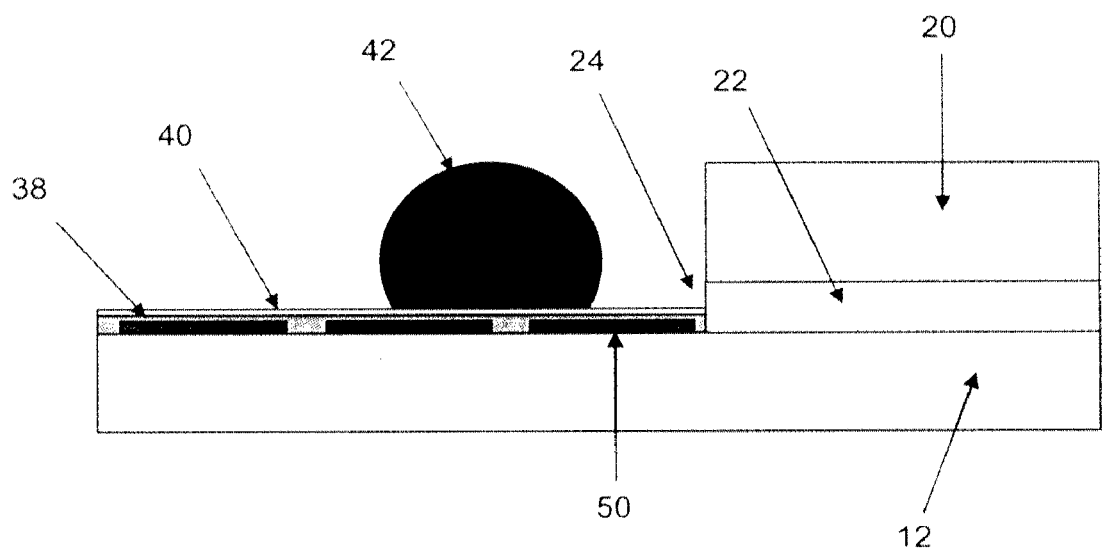
FIG. 2 shows a sectional view of a hybrid digital and channel microfluidic device in which a droplet is shown transported towards a channel opening.

FIG. 2 shows a section through device 10 in the vicinity of channel opening 24. While substrates 12 and 20 can be formed from a wide variety of materials, a preferred material for first 12 substrate is glass and a preferred material for second substrate 20 is poly(dimethyl siloxane) (PMDS). As shown in FIG. 2, electrodes are provided on first substrate 12 and are preferably formed by photolithography. Electrodes are preferably formed from chromium subsequently coated with a first dielectric layer 38. First layer 38 is preferably Parylene-C. Second layer 40 is preferably a hydrophobic material such as Teflon-AF®.

Droplets may be transported along the array by applying a voltage between adjacent electrodes. A preferred driving potential is in the range of about 100-300 $V_{RMS}$, and a preferred driving frequency is about 18 kHz (those skilled in the art will appreciate that DC voltages may also be used, although AC voltages may be preferred to reduce the possibility of hydrolysis occurring due to imperfections in the dielectric coating). Droplets preferably have a volume of 1-5 microliters, and more preferably, about 2.5 microliters (preferred droplet size is dependent on the electrode size).

Channel opening 24 is located in close proximity to final electrode 50. Accordingly, a droplet 42 transported along array to final array electrode 50 is brought into close contact with channel opening 24, and preferably is made to contact channel opening 24. Alternatively, multiple droplets may be transported to final electrode 50, whereby contact is made between the transported liquid and channel opening 24 only when a sufficient number of droplets have been transported to electrode 50.

Devices preferably have an overall thickness of several mm, and more preferably 1-3 mm and more preferably about 2 mm thick. Each substrate is preferably 0.5-1.5 mm thick and more preferably about 1 mm thick. Lateral dimensions of device 10 are preferably several mm to several cm. Access ports 32, 34 and 36 can be provided with a wide range of sizes, but are preferably 1-3 mm in diameter and more preferably about 1.5 mm in diameter. Access ports also provide locations for adding buffers or separation media to the channels. Array elements 14 are preferably about 1-3 mm$^2$, and more preferably about 2 mm$^2$, and preferably are spaced apart with an inter-electrode gap of 10-50 microns, and more preferably 25 microns. Channel dimensions are preferably adapted to provide laminar flow, and preferably are of sufficiently small size to promote the suction of external fluid via capillary action forces. Accordingly, those skilled in the art will readily appreciate that a wide range of cross-sectional diameters are compatible with various embodiments of the invention. Preferably, channels 22 and 26 have cross-sectional dimensions having a width of about 100 µm and a height of about 40 µm.

Although FIGS. 1 and 2 show a hybrid device comprising a single layer digital microfluidic array, those skilled in the art will readily appreciate that device 10 may comprise an additional substrate located above the array electrodes and separated from substrate 12 by a spacer layer (shown and discussed in a subsequent embodiment presented below).

Interfacing of DMF Array and Microfluidic Channel

Liquid from a droplet positioned at an electrode 50 adjacent to opening 24 may be introduced into channel 22 by one of many methods. Preferably, channel 22 is pre-filled with a liquid (such as a buffer or separation medium) and liquid from a droplet is transferred into opening 24 by electrokinetic flow. Electrokinetic flow may be achieved by applying a voltage, preferably a high voltage to achieve an electric filed (>100 V/cm) in the channel between an additional electrode downstream in channel 22 and another electrode placed within a droplet located at electrode 50.

Alternatively, if channel 22 is empty, liquid from a droplet located at electrode 50 may be transferred into channel 22 by capillary force. Accordingly, channel 22 may be filled by transferring multiple droplets to opening 24, where each droplet enters channel 22 via capillary action.

In yet another embodiment, a droplet delivered to a pre-filled channel 22 may be transferred by LaPlace pressure. However, for applications involving separation, particularly electrophoretic separation, electrokinetic injection is a preferred method of liquid transfer.

Methods of Fabrication of Hybrid Lateral Device

Although fabrication protocols for forming DMF and microchannel devices are well established, the present invention provides the first hybrid device in which a substrate comprising a DMF array is attached and adapted to be interfaced to a substrate containing a microfluidic channel. Accordingly, this new realm of microfluidics technology required significant experimentation and optimization of materials and chronology of fabrication steps.

For example, in initial development work, the inventors evaluated PDMS as a dielectric coating for digital microfluidics (in place of Parylene-C/Teflon-AF®), which facilitates straightforward bonding of microchannels. However, this method proved untenable for droplet movement because of the low breakdown voltage of PDMS (21 V/µm). Droplets actuated on devices formed in this manner frequently suffered from electrolysis.

The inventors therefore abandoned PDMS as a dielectric layer for the preferred combination of Parylene-C and Teflon-AF® discussed above. However, in initial experiments with these materials, it was discovered by the inventors that the application of the Parylene-C and Teflon-AF® coatings should occur after PDMS channels were bonded to the glass substrate.

Figure 3:
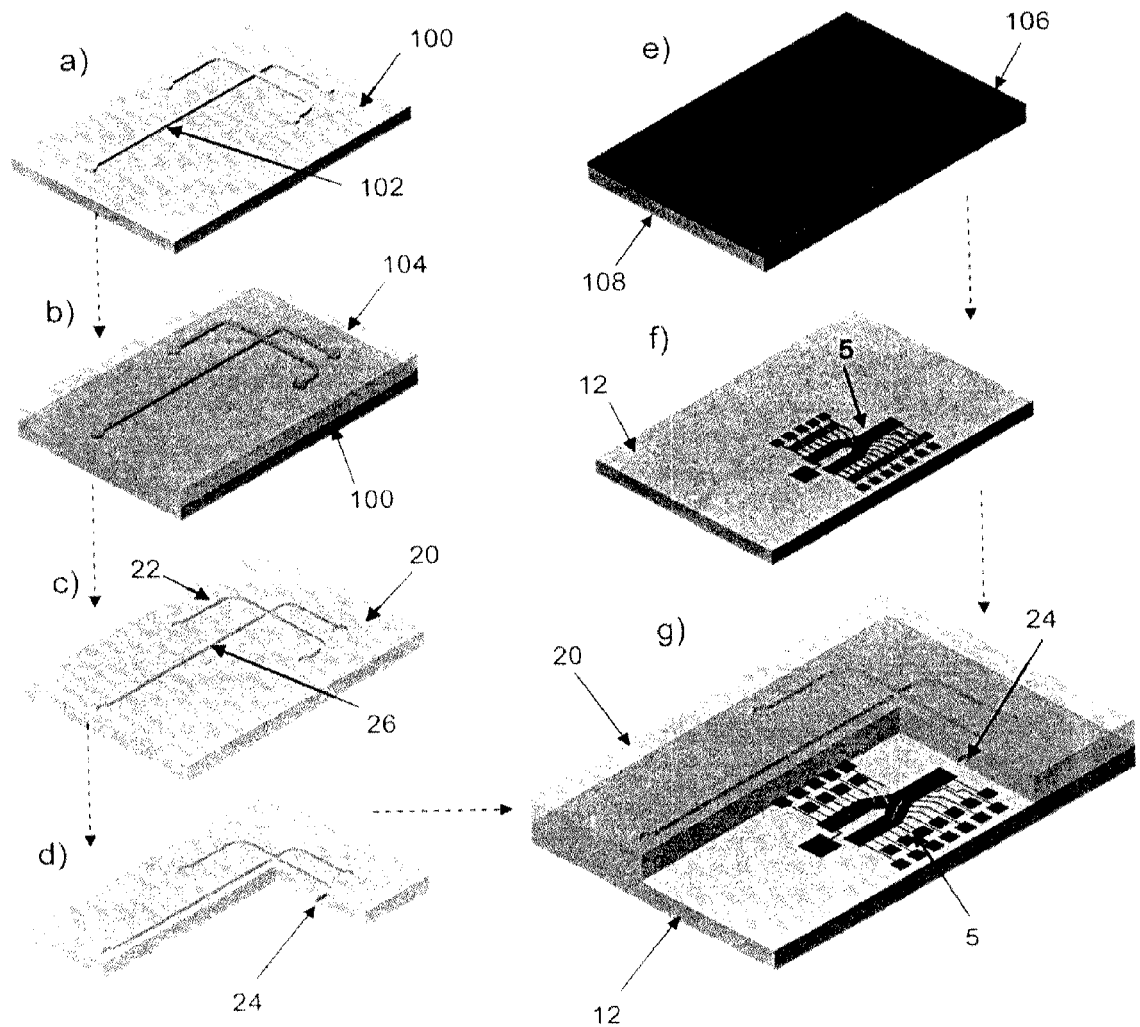
FIG. 3 schematically shows a preferred method for fabricating a dual substrate hybrid digital and channel microfluidic device.

Accordingly, a preferred sequence of fabrication steps is shown in FIG. 3. Initially, a channel master 100, preferably formed from SU-8, is provided with a channel ridge 102 formed thereon. The master is coated as shown in step b), preferably by casting with PMDS 104. After curing, the channel master 100 is removed in step c), and open channels 22 and 26 are obtained in a bottom surface of substrate 20. Those skilled in the art will appreciate that a wide variety of channel configurations are possible within the scope of the present invention. In step d), substrate 20 is cut to expose channel opening 24.

Substrate 12 is prepared in step e) by coating a glass substrate with a conductive layer 106 for forming the electrodes. Preferably, the conductive layer 106 is chromium. Photolithograph and etching are employed in step f) to provide digital microfluidic array 5 on the top surface of substrate 12.

The hybrid device is assembled in step g) in which substrate 20 incorporating microfluidic channels 22 and 26 is attached to the top surface of substrate 12 (without covering the digital microfluidic array 5). Substrate 20 is affixed to substrate 12 so that channel opening 24 is positioned adjacent to an electrode in array 5, as discussed above. Preferably, plasma bonding is performed for the adhesion of the substrates, for example, by exposure to an oxygen plasma for approximately 90 seconds.

As discussed above, the dielectric coatings 38 and 40 are preferably applied after affixing the two substrates to form the hybrid device. This adds a requirement that the channel access ports 32, 34 and 36 and channel opening 24 be protected with a blocking means (for example, by sealing with an adhesive tape) during application of the coatings (this step is not shown in FIG. 3). While it is possible that during this step, Parylene-C or Teflon-AF® may penetrate the protective seal (depositing on portions of the channel walls), the inventors found that this was not typical, as the electrokinetic characteristics of the microchannels were identical before and after coating, whenever tested.

Methods of Performing Separations with Hybrid Devices

Typically, there are two types of separations that are performed with microchannels: open channel separation and solid stationary support separation. The open channel mode is most common approach, with electrophoretic and micellar electrokinetic chromatography (MEKC) being among the most commonly used separation methods.

The hybrid digital and channel microfluidic device shown in FIGS. 1 and 2 is designed to perform a preferred separation protocol in which electrokinetic injection is employed at the intersection between channel 22 and second channel 26. Electrokinetic injection is performed by driving fluids by electroosmotic flow (EOF) across a channel intersection and subsequently injecting a discrete volume of analyte formed at the intersection down a longer "separation" channel. In the case of the present preferred embodiment, channel 22 is the initial channel, and channel 26 is the "separation" channel.

In a preferred embodiment, the separation channels are pre-loaded with a separation medium or buffer prior to injecting sample from a droplet. Pre-loading of the channels may be accomplished with a number of different methods, such as adding buffer or separation medium to access ports or reservoirs such as those shown in FIG. 1 at 32, 34 and 36.

In an alternative embodiment, one or more channels may be pre-loaded by droplet actuation on a digital microfluidic array residing on the hybrid device. Droplets of buffer or separation medium may be placed on the array, and transported to contact a channel opening by actuating the array. Channel loading is then preferably achieved through capillary forces drawing in liquid from the droplets. Preferably, a digital microfluidic array may provided to transport droplets to each access port or reservoir (alternatively, the hybrid device may include dedicated arrays for each port or reservoir), thereby feeding multiple channel openings or reservoirs. In one embodiment, multiple droplets may be transported to a given channel opening in a controlled manner while applying a separation voltage to the channel in order to reduce the susceptibility of the device to hydrostatic flows and/or evaporation.

Electric fields necessary for electrokinetic transport may be subsequently applied to channels 22 and 26 by the application of voltages between access port 34 and channel opening 24, and between access ports 32 and 36, respectively. Electrodes are preferably provided as platinum wires or contacts. Typically, a high voltage source is used to apply the required voltages.

Figure 4:
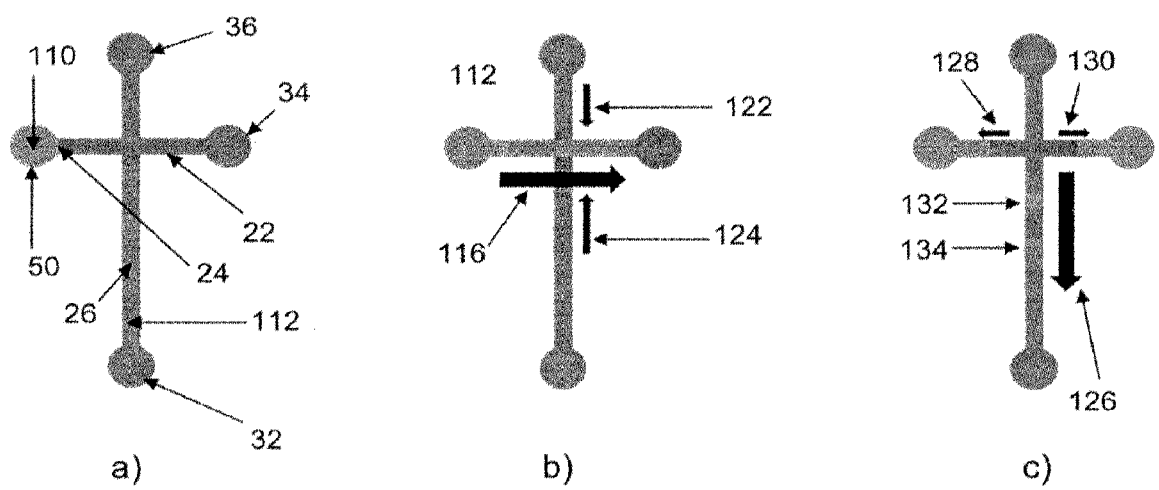
FIG. 4 shows a schematic of a dual channel separation device integrated into a hybrid digital and channel microfluidic device.

FIG. 4 schematically illustrates the process of electrokinetic injection and separation according to a preferred embodiment of the invention. For electrokinetic flow, also known as, electroosmotic flow the fluid in the channel is in direct contact with the electrodes for voltage driven flow. If there are two channels which intersect, as in embodiments 10 and 430 (discussed below), fluid can be driven across such an intersection and a defined plug may be injected. In FIG. 4a, channels 22 and 26 are shown as intersecting at intersecting point 28, and access ports 32, 34, and 36 are shown at channel ends. Final electrode 50 is shown located adjacent to channel opening 24. Droplet 110 is shown at electrode 50, having been transported by the actuation of digital microfluidic array 5, in fluid contact with channel opening 24. Channels 22 and 26 are pre-filled with a buffer or separation medium 112.

As shown in FIG. 4b, a portion 114 of the volume of droplet 50 is transferred into channel 22 and driven across channel 22 towards access port 36 under the action of an electric field shown at 116. Preferably, a high voltage HV is applied at access port 34, and ground potential GND is applied at channel opening 24. To form a "plug" via pinched injection at the channel intersection 28, intermediate voltages (i.e. between HV and GND) are empirically applied at access ports 32 and 36. The voltage conditions for such a "pinched" injection are outlined in FIG. 4 where the relative flows of fluid streams are denoted by arrows 116, 122, 124, 126, 128 and 130. Fluid residing in 50 is driven across the channel intersection to 34 by applying a high voltage (HV) to 50 and ground (GND) to 34. To "pinch" the loading stream of fluid, voltages are applied at 36 and 32 such that the voltage applied (V) is between HV and GND (HV<V<GND). Injection of a plug of the sample stream is then accomplished by quickly changing the voltages applied such that HV is applied to 36, GND to 32 and intermediate voltages to 50 and 34. Analytes in the injected plug can be subsequently separated into bands 132 and 134 by relative electrophoretic mobilities.

Following loading of channel 26 with a small volume of sample, the voltages are rapidly changed as shown in FIG. 4c. HV is applied to access port 36, ground to access port 32 resulting in a large electric field in channel 26 shown at 126, and intermediate voltage to access port 34 and channel opening 24, resulting in electric fields shown at 128 and 130. This acts to inject the plug (not shown) down separation channel 26. In this channel the plug of analytes are exposed to electroosmotic flow, acting to push all the analytes down the channel, and electrophoresis, acting to pull the analytes apart based on charge, and to some extent size. Bands of separated analyte are shown at 132 and 134.

It is important to note that in this method, only a small fraction of the fluid manipulated by the array (e.g. approximately 5 µL droplets) is sampled into the channels, and an even smaller fraction (<1 mL) is injected onto the separation column. In this capacity, the droplet serves an analogous role of a reservoir in conventional microchannel devices.

In other applications, however, it may be desirable to capture a large fraction of the processed droplet for analysis. In such cases, a solid phase extraction (SPE) element is preferably integrated into the sample channel. Injection of sample from separation is preferably achieved by capillary action at channel opening 124. For example, solid stationary supports can be integrated into the channel with monolithic stationary supports and packed beds of functionalize beads. The beads used are generally C-18 (a.k.a. octadecyl) functionalized silica beads. Solid phase extraction is achieved on the basis of loading the sample onto the column to trap it to the surface, washing the column and subsequently eluting the purified sample with a releasing agent (for example, with a high percentage of acetonitrile).

In further applications when analytes to be separated are similar in mass/charge ratio, it is desirable to use a solid phase support. Solid phase supports my be localized in the separation channel 26 by a variety of techniques, including, by not limited to, UV-curable porous polymeric monoliths (PPMs) or packed beds of functionalized beads. PPMs may be formed in situ by UV-initiated polymerization or acrylate/methacrylate monomers. Packed beds of beads may be formed by creating a frit or weir structure in the channel and then packing beads against the frit or weir. Such structures would allow for higher peak capacity separation of complex mixtures of analytes.

Hybrid Vertical Digital and Channel Microfluidic Device

Figure 5:
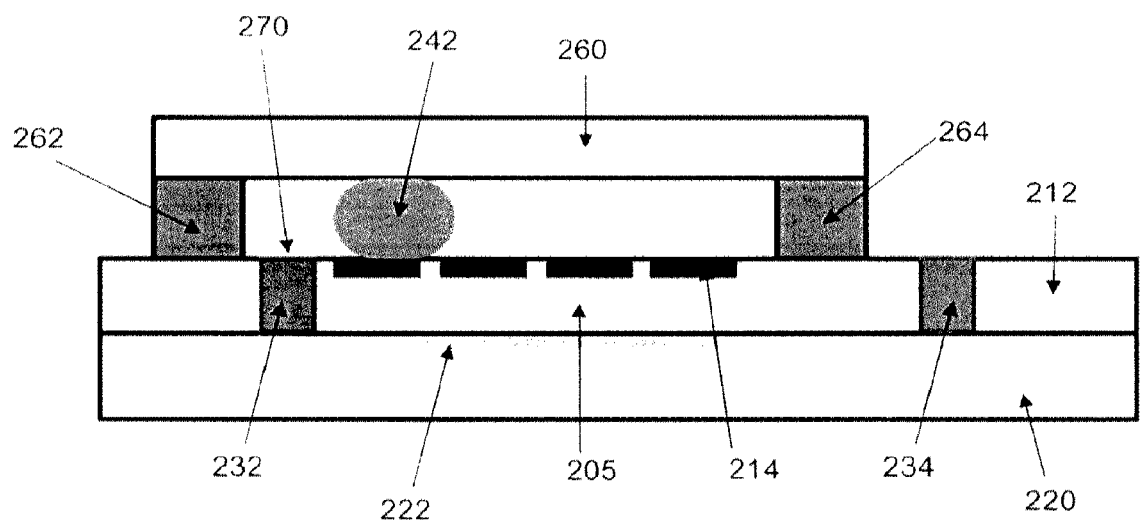
FIG. 5 shows a side view of a vertical hybrid digital and channel microfluidic device.

Although the aforementioned embodiment was shown in the context of a lateral hybrid device in which channel opening 24 is located adjacent to electrode 50 for droplet liquid injection into channel 22, another preferred embodiment includes a vertical arrangement of substrates. In this alternative embodiment of the invention, the lateral junction between the digital microfluidic array and the microfluidic channel is replaced with a vertical junction as depicted in FIG. 5. In this new format, droplets are manipulated on the top digital platform of the device, and are subsequently transferred to a microchannel network underneath, h through the vertical access holes.

This preferred embodiment is illustrated in FIG. 5, where substrate 212, having provided thereon a digital microfluidic array 5 with an array electrode shown at 214, is shown affixed above substrate 220, containing therein a microfluidic channel 222. Channel 222 is bounded by the contact between substrates 212 and 222. However, vertical port 232, extending through substrate 212, contacts channel 222 and forms a via between channel 222 and the upper surface of substrate 212. And additional vertical port 234 is also provided, which allows external access to channel 222. The device preferably further includes an optional cover layer 260 that preferably comprises a transparent conductive material such as indium tin oxide. Cover layer 260 may accordingly form an upper electrode plane for actuating the digital microfluidic array. Cover layer is preferably supported above substrate 212 by an electrically insulating spacer layer (shown at 262 and 264 in FIG. 5), thereby forming a planar gap for droplet transport on array 5.

As further shown in FIG. 5, droplets 242 may be actuated on upper surface of substrate 212 by array 5. Droplet 242 may be transported adjacent to well opening 270, where it is preferably captured by a hydrophilic capillary force and drawn into access port 232. Fluid may subsequently enter microfluidic channel 222 by one of several means, including, but not limited to, external pumping, (e.g. by creating a pressure differential relative to access port 234), capillary forces, and electrokinetic forces (as outlined in preceding embodiments).

Figure 6:
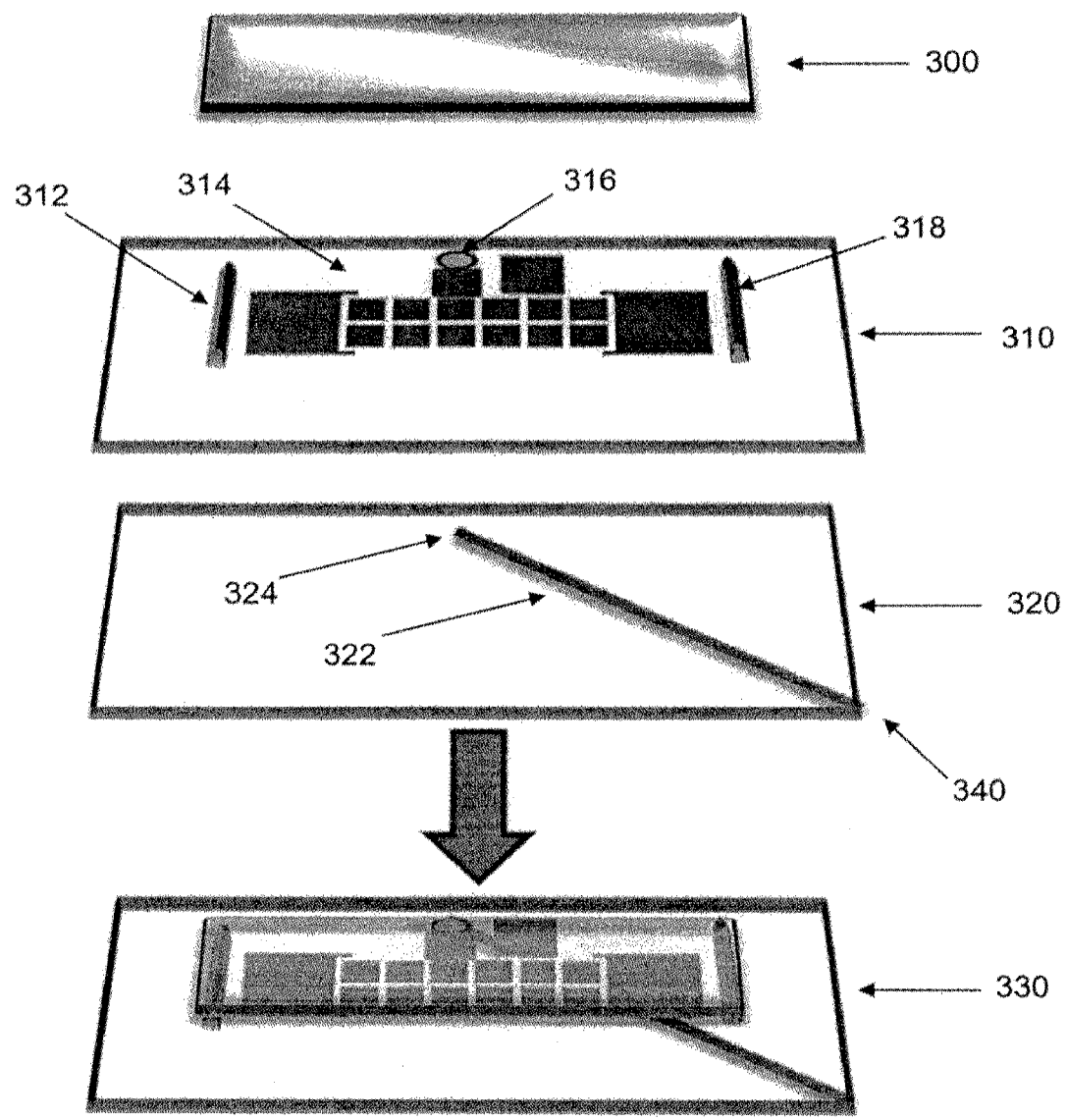
FIG. 6 shows the components and assembly steps of a preferred vertical hybrid digital and channel microfluidic device incorporating a single channel.

FIG. 6 shows an exploded schematic of the device design, highlighting the three layers used in fabrication and their assembly. Layers 300 and 310 define the DMF platform (on top), and layers 310 and 320 define the microchannel network (below). Specifically, layer 300 is preferably a transparent conductive material such as indium-tin-oxide (ITO) coated glass slide that forms a transparent upper electrode. Layer 310 comprises a digital microfluidic array 314, spacers 312 and 318 for the ITO cover plate, and well 316 for vertical droplet transport. Layer 320 has formed in its top surface a microfluidic channel 322 extending from an intermediate portion to a corner, where an external opening is formed when layer 320 is capped by layer 310, for example, comprising an electrospray ionization tip 340. Furthermore, the proximal end 324 of channel 322 is located in position that is directly beneath the corresponding lateral location of well 316 in layer 310. When all layers are joined to produce the hybrid digital and channel microfluidic device 330, well 316 is aligned with proximal end 324 of channel 322. Accordingly, droplets actuated by array 314 may be contacted with well 316, drawn into well 316 by capillary forces, and contacted with channel 322.

Figure 7:
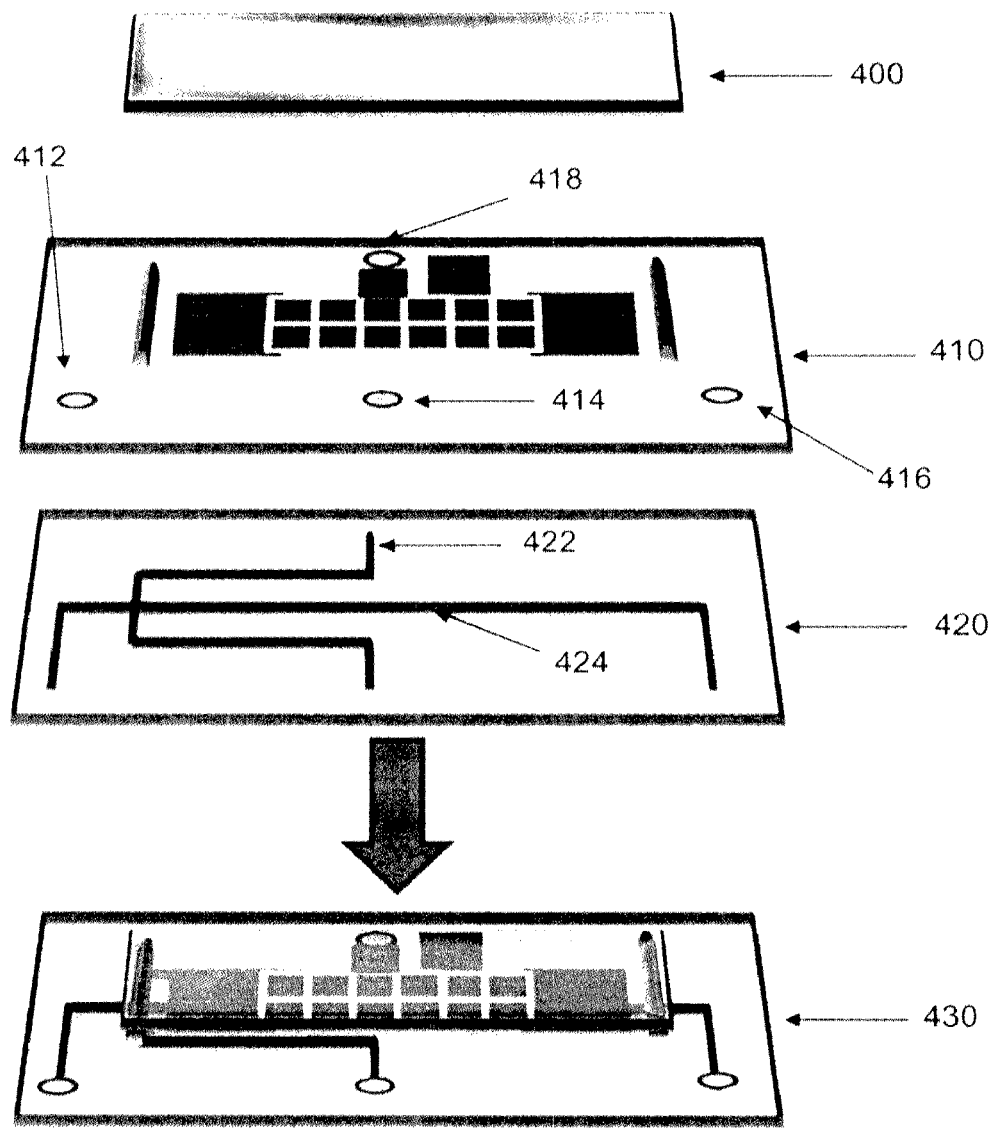
FIG. 7 shows the components and assembly steps of a preferred vertical hybrid digital and channel microfluidic device incorporating a channel network for separation applications.

Another embodiment showing a vertical hybrid device adapted for a separation process is illustrated in FIG. 7, in which layer 410 further includes access ports 412, 414 and 416 that play a role that is analogous to access ports 32, 34 and 36 in FIG. 1. Access ports 412, 414 and 416 are positioned to align with ends of microchannels 422 and 424 in layer 420, thereby providing locations for inserting electrodes for initiating electroosmotic flow and electrophoretic separation, and also providing a location for optionally introducing buffers or separation media into channels 422 and 424. Hybrid device 430 functions in a manner analogous to that of the device shown in FIG. 1, with the primary difference being that the sample is introduced into channel 422 vertically via well 418 rather than laterally via direct droplet contact with the microfluidic channel.

Figure 8:
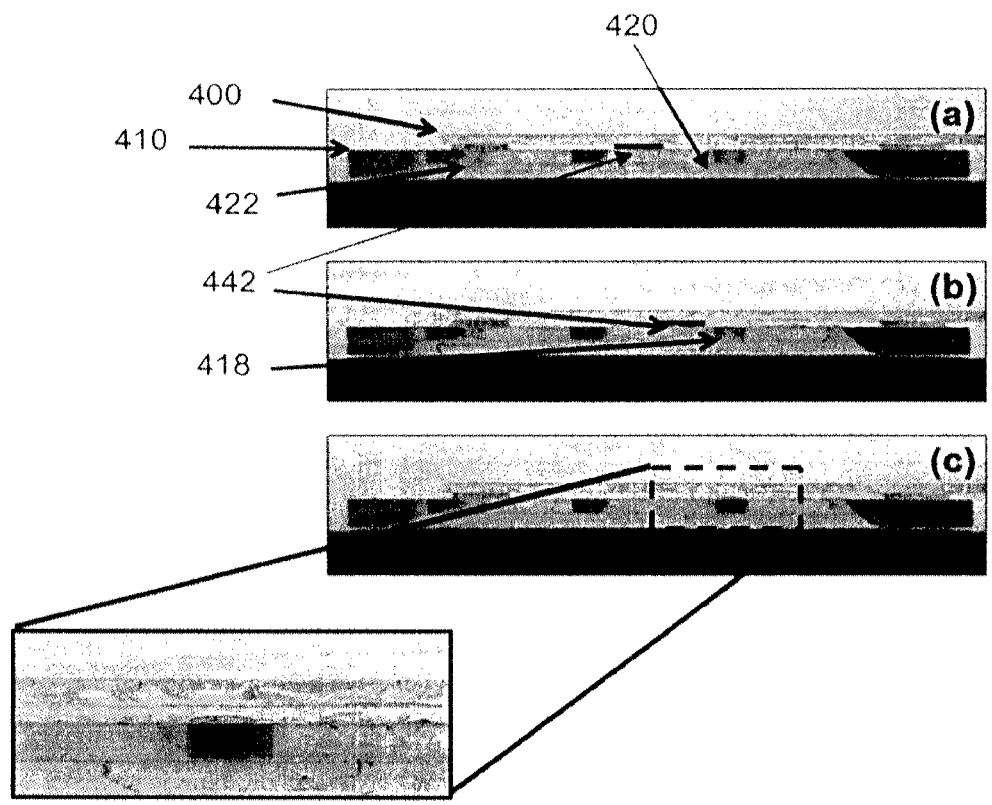
FIG. 8 shows photographs of a fabricated vertical hybrid digital and channel microfluidic device, in which a droplet is shown transported to a vertical well.

FIG. 8 is a series of photographs illustrating the process of sample transfer from the digital microfluidic platform to the microchannel platform for the embodiment shown in FIG. 7. In FIG. 8a, layers 400, 410 and 420 are clearly shown, along with microfluidic channel 422. Droplet 442 is shown in FIG. 8a, and is transported closer to well 418 via digital microfluidic array electrodes (not shown) in FIG. 8b. In FIG. 8c, droplet has been transported by the actuation of digital microfluidic array to come into contact with well 418, where it is drawn into well 418 and contacted with microfluidic channel 422.

A portion of the sample droplet in the well may subsequently be inserted into the channel network using electrokinetic injection, as described above with regard to the lateral hybrid device. For example, electrodes (such as the platinum contacts or wires) may be provided in access ports or reservoirs, allowing the application of a voltage for electrokinetic injection.

The preceding lateral and vertical device embodiments, and methods of operation described herein, are provided to disclose preferred embodiments of the invention. Those skilled in the art will readily appreciate that a wide range of modifications and adaptations of the embodiments and examples provided herein are further contemplated by the invention and are incorporated within its scope. The operation of the hybrid microfluidic device in the geometries described herein is designed to fully exploit the sample preprocessing ability of digital microfluidics prior to sample separation, or other analytic process, such as mass spectrometry. Most notably, sample preparation is integral to analysis of biological samples (e.g. fluids, cells or tissues) due to the underlying complex matrix of the sample. Matrix effects are substantially reduced when the sample is processed prior to analysis. This allows for samples of higher informing power to be introduced to the microchannel platform for chemical separation and/or mass spectrometry analysis. Therefore, the digital microfluidic array of the hybrid digital and microfluidic device may be further adapted to include additional digital microfluidic sample preparation systems known in the art without departing from the scope of the present invention.

The present invention will now be illustrated by the following non-limiting examples.

EXAMPLE 1

Figure 9:
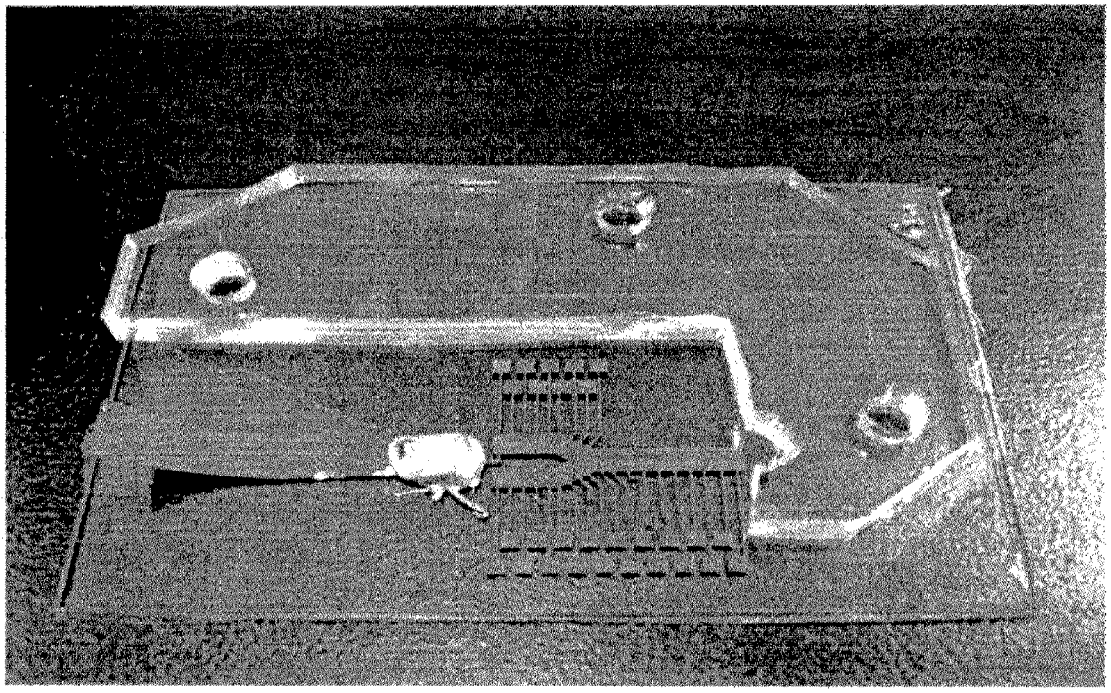
FIG. 9 shows a photograph of a fabricated lateral hybrid digital and channel microfluidic device.

Fabrication of Lateral Hybrid Digital and Channel Microfluidic Device: Materials Materials required for device fabrication included chromium pellets (Kurt J. Lesker Canada, Toronto, ON), hexamethyldisilazane (HMDS) (Shin-Etsu MicroSi (Phoenix, Ariz.), Shipley S1811 photoresist and MF321 developer (Rohm and Haas, Marlborough, Mass.), CR-4 chromium etchant (Cyantek, Fremont, Calif.), AZ300T stripper (AZ Electronic Materials, Summerville, N.J.), PARLYENE-C (Specialty Coating Systems, Indianapolis, Ind.), and Teflon-AR®1600 (DuPont, Wilmington, Del.). Materials for microchannel fabrication included SU-8-25 photoresist (MicroChem, Newton, Calif.), silicon wafers (Waferworld, West Palm Beach, Fla.), and polydimethylsiloxane (PDMS) (Sylgard-184 kits, Dow Corning, Midland, Mich.). Several fabrication protocols were evaluated for forming a lateral hybrid digital-channel microfluidic device. A preferred is described below. Digital microfluidic elements (electrodes) were formed from chromium (150 nm) on glass substrates in the University of Toronto Emerging Communications Technology Institute (ECTI). An array of electrodes was patterned by photolithography and wet etching in a "Y-shape" with electrode dimensions of 1 mm×1 mm in the branches and 1.2 mm×1.2 mm in the stem, with inter-electrode gaps of 25 µm. The microchannel network was formed by soft lithography, casting poly(dimethyl siloxane) (PDMS) against an SU-8-on-silicon master in a method similar to that reported by Duffy et al.[31] The channels were 40 µm deep×100 µm wide, and the layout included a cross element for injection and a 4.5 cm-long separation channel. The device is shown in FIG. 9.

After curing, holes were punched at the channel inlets to create fluid reservoirs in the ~3-4 mm~thick PDMS slab. The sample channel was exposed as depicted in FIG. 2 by slicing through the slab with a scalpel. The microchannel network was then bonded to the glass substrate carrying the electrode array after exposure to an oxygen plasma[31] (90 sec) such that the sample channel inlet mated with the edge of the electrode array—this formed the "digital-channel interface." Channel inlets were then covered with low-tack dicing tape (Semiconductor Equipment Corporation, Moorpark, Calif.), and a layer of PARLYENE-C (2 µm) was deposited on the electrode array. A hydrophobic coating of Teflon-AF® (50 nm) was applied by spin coating (2000 rpm, 1 min) followed by baking on a hot plate (160° C., 10 min). The dicing tape was removed when the device was ready for use.

EXAMPLE 2

Preliminary Testing of Lateral Device

Unless otherwise indicated all general-use chemicals were obtained from Sigma-Aldrich (Oakville, ON). In testing the device, droplets containing reagents were moved, merged, incubated (if needed), and then delivered to the channel network for separations. Droplet movement was facile and fast, facilitating rapid mixing of a wide range of samples, reagents, and buffers. Pluronic solution additives were used to limit non-specific adsorption and pinning to the surface and for long incubation times (>1 min), evaporation was minimized by enclosing the droplet under a PDMS cover.

Figure 10:
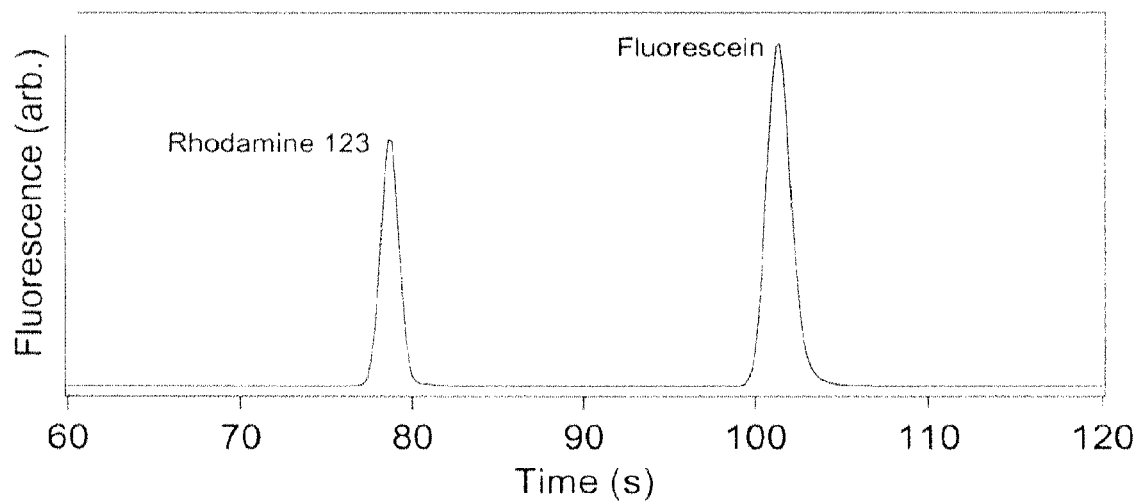
FIG. 10 shows an electrochromatogram obtained by separating rhodamine 123 and fluorescein using a hybrid lateral device.

In initial experiments, the interface device was evaluated using a simple mixing experiment, separate droplets containing rhodamine 123 or fluorescein were moved and merged, and the combined droplet was sampled into the channels, by electrokinetic flow, for separation by micellar electrokinetic chromatography (MEKC). Typical separation data is shown in FIG. 10. Clearly, the original droplets were mixed, and both analytes were detected in the electrochromatogram. When evaluated in replicate trials, the method was characterized by excellent retention time reproducibility (<1% RSD) and separation efficiency (nearly 500,000 theoretical plates per meter), but the relative peak area variation was larger than expected (~7% RSD).

Figure 11:
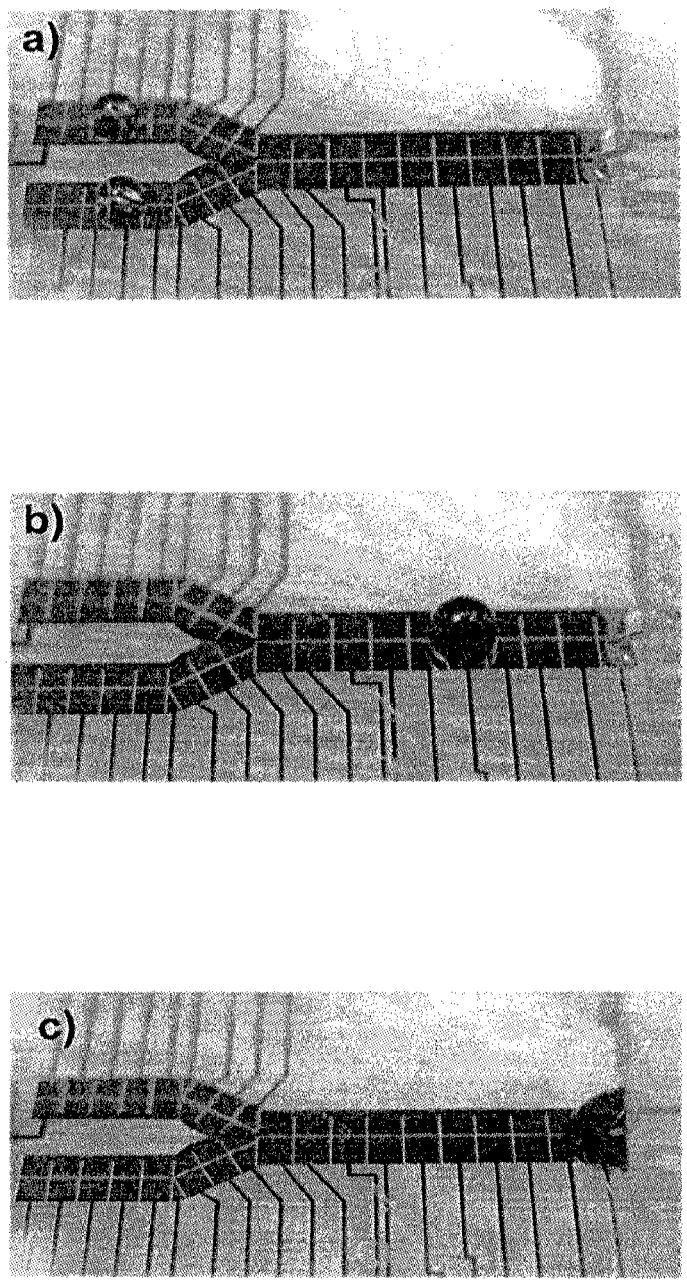
FIG. 11 shows successive frames from a movie demonstrating the transport of a droplet along a digital microfluidic array to a microfluidic channel on a hybrid device.
Figure 12:
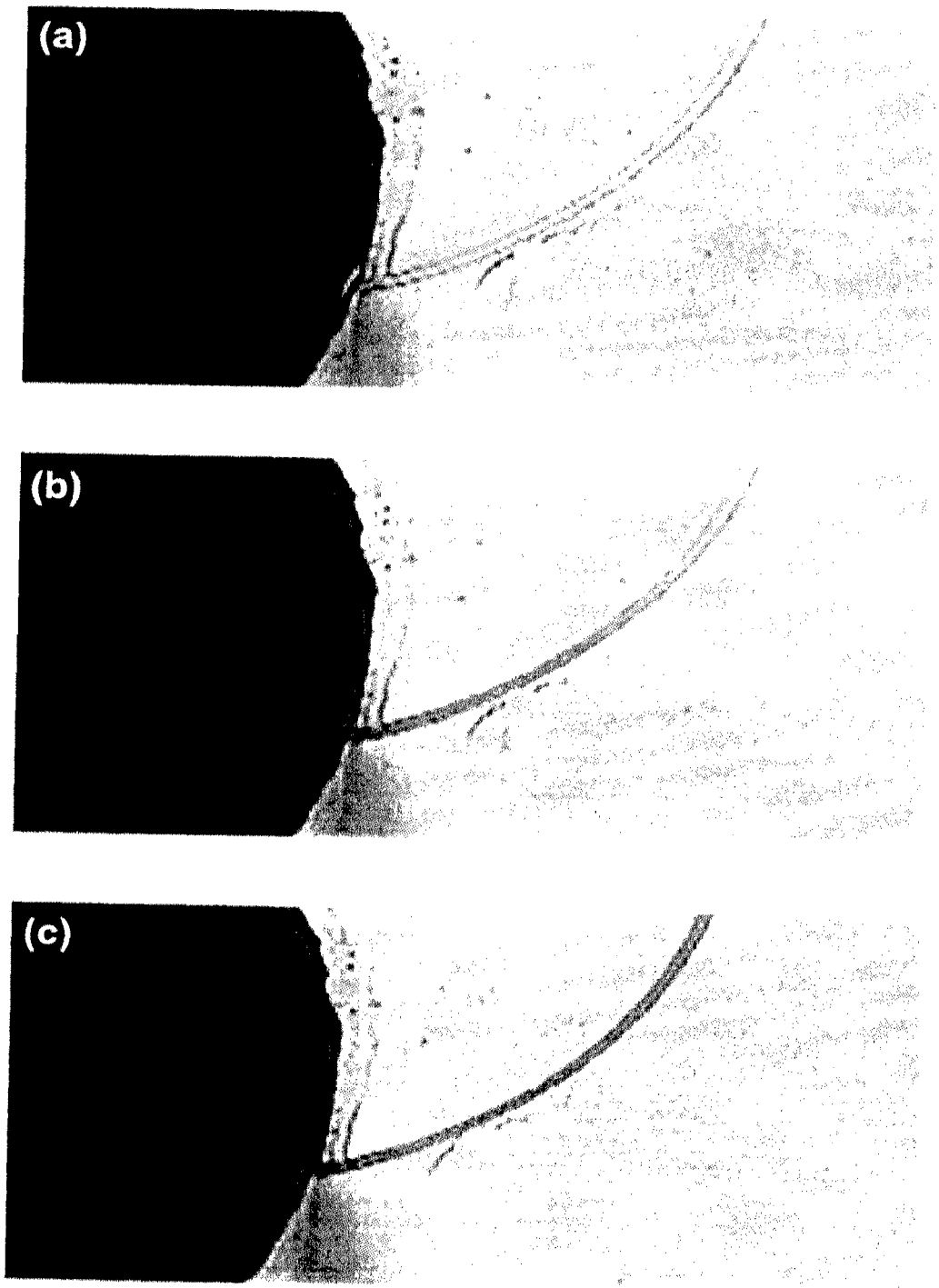
FIG. 12 shows successive frames from a movie demonstrating the transfer of liquid from a droplet to microfluidic channel on a hybrid device.

The principle of device operation is shown in FIGS. 11a to 11c which shows a picture, schematic, and frames from movies depicting a hybrid digital-channel microfluidic device. The figures show frames from a movie depicting droplets containing food coloring dyes being moved, merged, and mixed by DMF and then delivered to the interface. In FIGS. 12 (a-c), frames from a movie demonstrate electrokinetic loading of the contents of a droplet into a microchannel.

The fluorescent dyes, rhodamine 123 and fluorescein were used to evaluate separation performance and reproducibility. Samples containing both dyes (10 µM each, final concentration) were prepared (a) on-chip by merging droplets (as described above), (b) off-chip in five independently prepared samples, and (c) off-chip from a single mixture. In each case, five replicates were loaded electrokinetically into microchannels and then separated by MEKC in run buffer 1. The resulting electrochromatograms were analyzed for peak area, retention time ($t_R$) and peak width at half-max ($W_{1/2}$) using PeakFit (SeaSolve Software Inc., Framingham, Mass.). For each run, the rhodamine 123 peak area was calculated relative to that of fluorescein and is listed as a percent relative standard deviation (% RSD). The number of theoretical plates, N, was calculated using $W_{1/2}$.

$$N = 5.54 \left( \frac{t_R}{W_{1/2}} \right)^2$$

The first control (called "individual samples"), implemented to determine the variance caused by sample dispensing (i.e., pipetting the two dye solutions), involved replicate measurements made from five individually prepared samples. Each sample contained run buffer (45 µL), rhodamine 123 and fluorescein (2.5 µL each). The second control (called "common sample"), implemented to determine the variance caused by mixing, injection, and separation, involved replicate measurements from a single mixture of the two dyes.

In comparing the performance of the on-chip method to the two controls, it appears that the primary source of peak area variance is sample dispensing (i.e., manual pipetting of droplets to the device surface). As listed in Table 1, the peak area reproducibility in the "individual samples" control is similar to that observed for the on-chip method, suggesting that the on-chip method and this control share the primary source of variance. In contrast, the peak area reproducibility in the "common sample" control is significantly improved, suggesting that the contribution to variance from mixing, injection, and separation, is much lower. Thus, we speculate that in future experiments with on-chip dispensing from reservoirs (instead of pipetting to the surface), the peak area reproducibility of the on-chip method will be substantially improved. Regardless, the performance reported here is impressive (particularly the retention time reproducibility), considering the novelty of this technique.

TABLE 1

Results from Preliminary Mixing Experiment

| | Retention Time % RSD | Normalized Area[a] % RDS | Efficiency (N/m) |
|---|---|---|---|
| On-Chip | | | |
| Rhodamine[b] | 0.83 | 6.67 | 477726 |
| Fluorescein | 0.99 | 6.98 | / |
| Aliquots from Common Sample | | | |
| Rhodamine | 1.25 | 1.62 | 408822 |
| Fluorescein | 1.29 | 1.59 | / |
| Separate Prepared Mixtures | | | |
| Rhodamine | 1.71 | 8.44 | 405942 |
| Fluorescein | 2.09 | 9.36 | / |

EXAMPLE 3

On Chip Processing and Cell Lysate Assay Performed on Lateral Device

For on-chip processing materials were obtained from Sigma-Aldrich (Oakville, ON) and for cell lysate assay materials were obtained from American Type Culture Collection (ATCC, Manassas, Va.) unless otherwise indicated. Additional reagents used in on-chip processing included methanol and acetonitrile (ACP, Montreal, QC), fluorescein isothiocyanate monolabeled insulin (FITC-Ins) from Invitrogen-Molecular Probes (Eugene, Oreg.), and food coloring dyes from McCormick Canada (London, ON). Additional reagents used in cell culture experiments included fetal bovine serum and Trypan blue dye from Invitrogen Canada, (Burlington, ON).

HeLa cells were grown in a humidified incubator (5% $CO_2$, 37° C.) in Dulbecco's Modified Eagle Medium (DMEM) supplemented with fetal bovine serum (10%), penicillin (100 IU $mL^{-1}$), and streptomycin (100 µg $mL^{-1}$). Cells were subcultured every 3-4 days at ~5×10³ cells $cm^{-2}$ seeding density. For lysis, cells were washed in phosphate buffered saline (PBS), then suspended (2×10⁶ cells $mL^{-1}$) in lysing medium containing PBS with Pluronic F-68 (0.02% wt/v), Triton X-100 (1%), and PMSF (1 mM). After incubation on ice (30 min), the lysate was centrifuged (1250 g, 5 min) and the supernatant was collected and stored in a freezer (−85° C.) until use.

Amino acid standards and cell lysate were labeled on-chip with the fluorogenic dye, naphthalene 2,3-dicarboxyaldehyde (NDA) using potassium cyanide (KCN) as nucleophile. In these experiments, two solutions were used, containing the analytes and the label, respectively. For on-chip labeling of amino acids, the former solution comprised glycine, alanine and valine standards (20 µM each with 4 mM KCN in run buffer 2), while the latter comprised NDA (2 mM in run buffer 2). For on-chip labeling of cell constituents, the analyte solution was formed by diluting a thawed aliquot of lysate 1:10 in run buffer 1 with KCN (20 mM final conc.), while the reagent solution was NDA (10 mM) in neat acetonitrile. In each case, droplets of analyte and reagent solution were moved, merged, incubated (5 min), and then delivered to the digital-channel interface by DMF. Samples were then loaded and injected electrokinetically, followed by a separation using MEKC in run buffer 1 (lysate) or 2 (standards).

Lysate peaks were tentatively identified by standard additions of NDA-labeled amino acids. Briefly, amino acid standards (50 µM) were reacted off-line with KCN (2 mM) and NDA (1 mM) in borate buffer (50 mM, pH9, 30% ACN). Lysate was labeled off-line using the same concentrations described above and diluted 1:10 in run buffer 1 prior to analysis. Aliquots of lysate (48 µL) were combined with aliquots of amino acid standards (2 µL) and separated by MEKC in run buffer 1 to identify co-eluting lysate analytes.

EXAMPLE 4

On Chip Processing and Cell Lysate Assay Performed on Lateral Device: Results

Prior to experiments, which all involve the device shown in FIG. 9, the network of microchannels was loaded with run buffer by filling one reservoir (50 µL) and gently applying positive pressure. After filling the channels, buffer was added to the reservoirs to achieve identical fluid heights to avoid hydrostatic flow. Gentle pressure was applied, with a rubber Pasteur pipet bulb, to the run buffer reservoir, creating a small outward meniscus of fluid at the digital-channel interface. Devices were used as described above, or, in some cases, supplemented with an additional buffer volume (45 µL) pipetted adjacent to the interface to balance the flow. Platinum wire electrodes (250 µm dia.) were inserted into each buffer reservoir as well as into the interface; the latter was pushed through the PDMS slab to hold it in place. After preparing the microchannel platform, droplets (2.5 µL) were actuated by DMF in single-plate format. Driving potentials (100-300 $V_{RMS}$, 18 kHz) were generated by amplifying the output of a function generator and were applied to sequential pairs of electrodes to move, merge, and mix droplets. Droplet actuation was monitored and recorded by a Hitachi CCD camera mated to an imaging lens (Edmund Industrial Optics, Barrington, N.J.).

After delivering a droplet to the interface by DMF, the contents were driven into the sample channel electrokinetically for pinched injections and separations. Electric fields were applied via a high voltage sequencer (LabSmith, Livermore, Calif.), and separations were performed in micellar electrokinetic chromatography (MEKC) mode in run buffer 1 (20 mM Borate pH 9.0, 50 mM SDS and 10% ACN) or run buffer 2 (20 mM borate pH 9.0, mM SDS, 30% ACN). Analytes were detected by laser induced fluorescence using an inverted microscope (Olympus IX-71) mated to an argon ion laser (Melles Griot, Carlsbad, Calif.). The 488-nm laser line was used for green fluorescence (fluorescein, rhodamine and FITC-Ins), and the 457-nm line was used for blue fluorescence (NDA-derivatives). The laser was focused into the channel using an objective (60×); the fluorescent signal was collected by the same lens and filtered optically (536/40-nm band pass and 488-nm notch filter for green fluorescence and a 482/35-nm band pass and 457-nm notch filter for blue fluorescence) and spatially (500 µm pinhole) and imaged onto a photomultiplier tube (Hamamatsu, Bridgewater, N.J.). PMT current was converted to voltage using a picoammeter (Keithley Instruments, Cleveland, Ohio) and then collected using a DAQpad A-D converter (National Instruments, Austin, Tex.) and a PC running a custom LabVIEW (Natl. Inst.) program.

Figure 13:
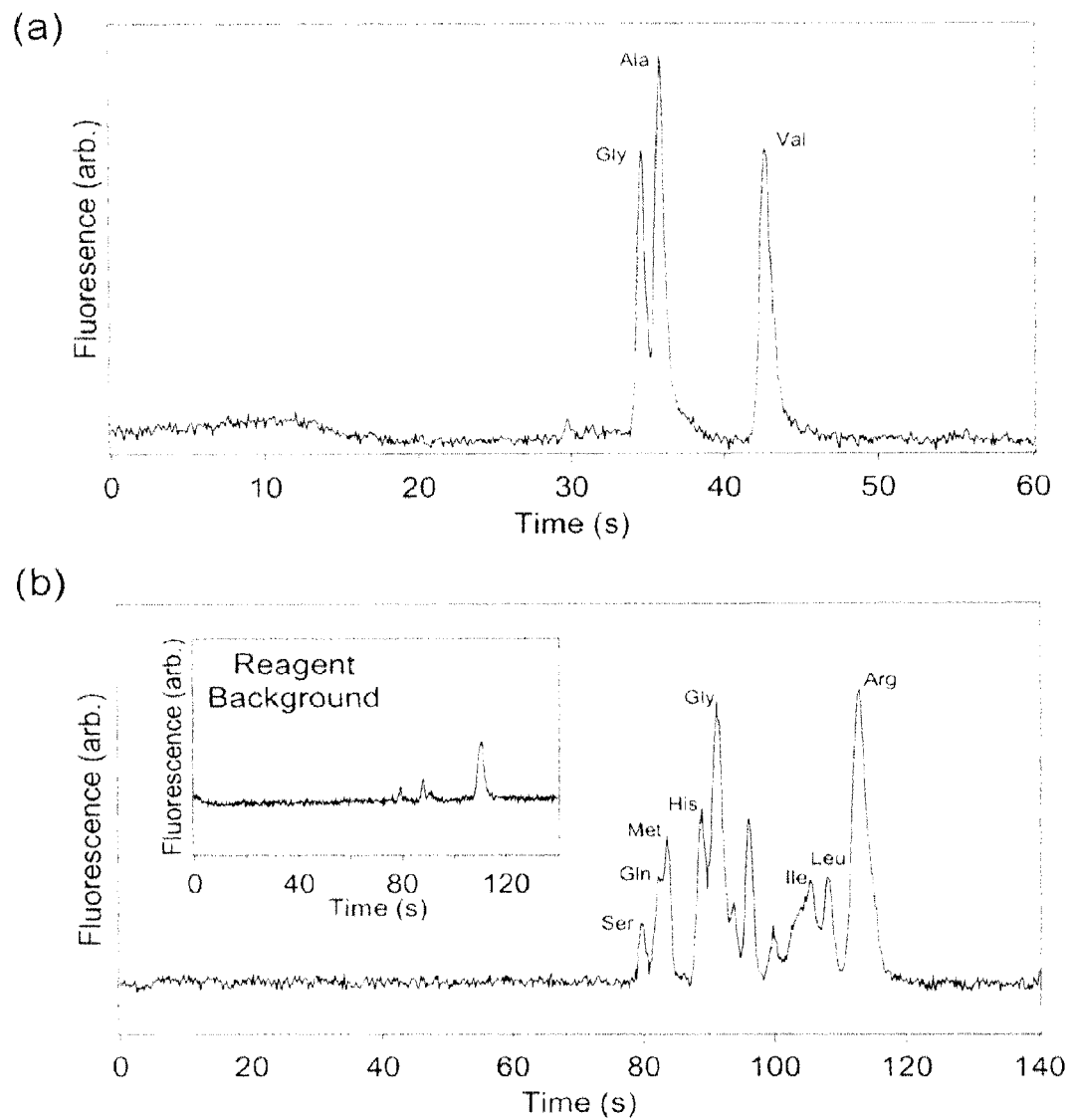
FIG. 13 shows elecrochromatograms generated after on-chip NDA labeling of amino acids and cell lysate: (a) Glycine (Gly), alanine (Ala) and valine (Val) (10 μM ea.) were labeled with NDA for five minutes and then injected and separated by MEKC; (b) HeLa cell lysate labeled with NDA for one minute and then separated by MECK; the inset to (b) was generated using an identical protocol, but with no lysate, and the Y-axis was scaled identically to that of the main panel. Peaks were assigned by spiking with NDA labeled standards.

To demonstrate the utility of the new device for integrated sample processing, it was used to fluorescently label amino acid standards and cell lysate on-chip, followed by separations. For the former, a droplet containing the fluorogenic reagent, NDA, was merged with a droplet containing a mixture of three amino acid standards, glycine (Gly), alanine (Ala) and valine (Val), on the digital platform. The merged droplet was actuated between adjacent electrodes to mix its contents for ~2 min (comparable to reaction times reported for NDA labeling in microchannels[3]) and then was delivered to the interface where its contents were sampled into the channel by EOF. FIG. 13a shows an electrochromatogram generated using this method. Under these conditions, the three species separate in less than one minute.

A similar on-chip protocol was used to label the amines in a solution of cell lysate. As shown in FIG. 13b, the constituent peaks are partially resolved in less than two minutes, and several of the peaks were tentatively assigned by spiking lysate mixtures with NDA-labeled amino acid standards. As expected, the more hydrophobic amino acids (e.g., leucine) migrated slowly because of interaction with the micelles. Basic species such as arginine were likewise slowed as a function of electrophoretic migration in the opposite direction of the cathodic EOF.

EXAMPLE 5

Demonstration of Tryptic Digestion on Lateral Device

To demonstrate a second sample processing application for the new device, it was used to digest a proteomic analyte prior to separation. Singly tagged FITC-Insulin (FITC-Ins) was a useful model for this work, as the single label simplifies the number of detectable species.

Two solutions were used for evaluation of on-chip digestion: FITC-Ins (50 µg/mL) in borate buffer (50 mM, pH 9), and trypsin (100 µg/mL) in Tris-HCl buffer (10 mM, 1 mM $CaCl_2$, 0.08% pluronic F-127, pH 8.5). Droplets of each solution were moved, merged, and mixed by DMF, and allowed to react for a designated period of time (1, 5, 15, and 30 min). During incubation, to limit the effects of evaporation, the reacting droplet was enclosed in a PDMS cover. After reaction, the processed insulin was delivered to the digital-channel interface by DMF, and loaded, injected, and separated by MEKC in run buffer 1. Upon injection into the channels, the reaction was immediately quenched, as the surfactant denatures the enzyme; thus, this serves as a metric for monitoring reaction progress as a function of time.

Figure 14:
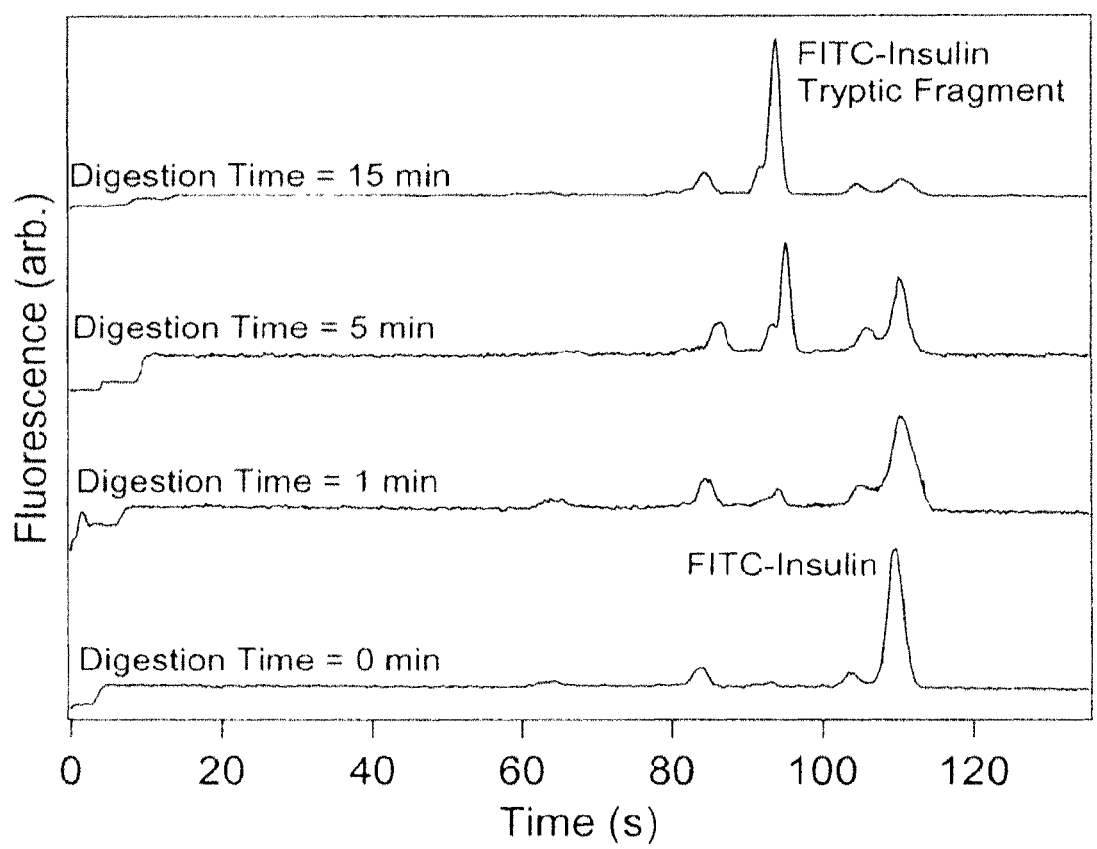
FIG. 14 shows electrochromatograms generated by on-chip digestions of singly labeled FITC-Insulin (offset vertically for clarity).

FIG. 14 shows four electrochromatograms generated after progressively longer digestion times. As shown, as digestion time increases, the primary FITC-Ins peak (retention time ~110 s) disappears, while a new peak belonging to a digest fragment appears at retention time ~94 s.

Tryptic digestion of FITC-Ins can create two labeled fragments through cleavage at the B-Chain Lys or B-Chain Arg residues forming peptides that are 1- or 8-residues shorter than the parent molecule. The digest fragment peak in the electrochromatograms appears to have a shoulder which may correspond to detection of both fragments. Overall, the time required for complete digestion (~15 min) is short relative to conventional solution-phase digestion protocols which require longer times (~12 hours) and elevated temperature (37° C.). These results show devices with much larger electrode arrays for integration of multistep proteomic processing regimens can be readily constructed.

EXAMPLE 6

Fabrication of Vertical Hybrid Digital and Channel Microfluidic Device

Microchannels were fabricated by patterning a glass substrate using photolithographic techniques followed by wet etching with dilute hydrofluoric acid. Following etching a clean slide is marked, drilled and then aligned with the etched slide. The device is then thermally bonded together in a furnace at high temperature. To create the DMF device on top of the microchannel device the following protocol was performed:
1) Evaporate chromium (Cr) on the glass surface.
2) Spin-coat the surface with positive photoresist.
3) Expose the resist to UV light using a photomask of the electrode design (the photomask was provided as a thick transparency film printed at 12,000 dpi).
4) Develop the resist to remove that which was exposed to light.
5) Etch the now exposed chromium that surrounding the desired pattern.
6) Remove the remaining photoresist with photoresist stripper.
7) Cover all of the channel access holes with dicing tape and then coat the device with an insulating dielectric (Vapor deposited Parylene-C, 2.5 um) and a hydrophobic layer (spin coat 1% wt/wt Teflon-AF® solution in FC40 oil, 50 nm)
8) Remove the dicing tape.
9) Insert fluid reservoirs into the non-interface access holes.
10) Insert and secure thin platinum (Pt) wires to the device such that they will contact fluids in the reservoirs and the processed sample, once it is transferred into the interface well. It is noted that the electrode for the well is hooked and hangs over the edge of the well to make electrical contact with the processed sample when it is introduced to the well. The Pt does not touch the array droplets and only comes in contact with fluid when it is transferred to the well.

EXAMPLE 7

Figure 15:
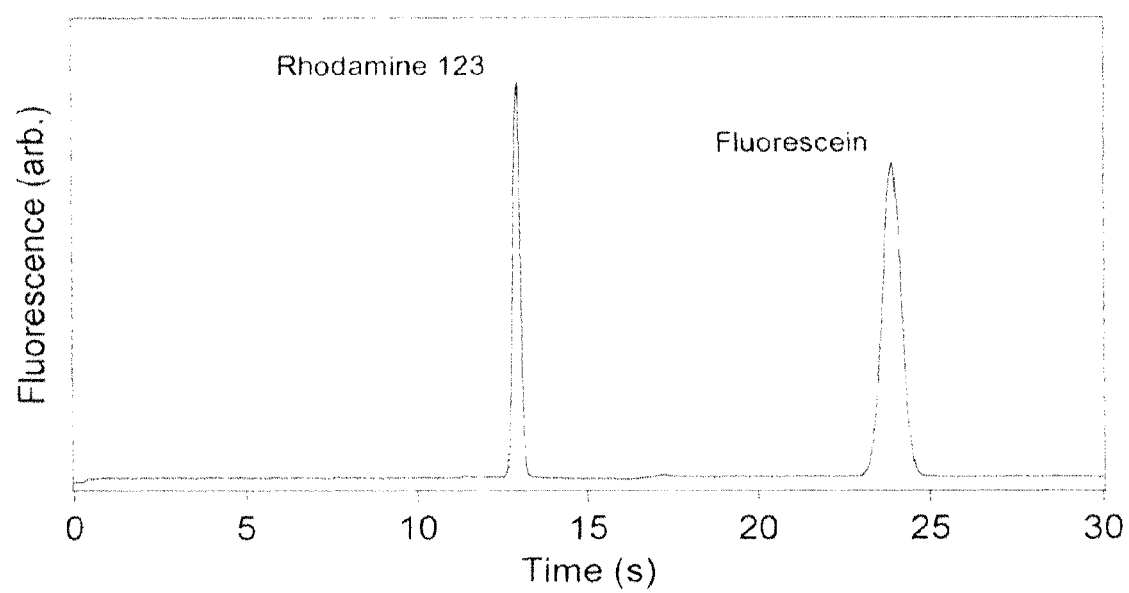
FIG. 15 shows an electrochromatogram obtained by separating rhodamine 123 and fluorescein using a hybrid vertical device.

Demonstration of Vertical Hybrid Device for Separation and Mass Spectrometry Sample Preparation In this example, the vertical hybrid digital and channel microfluidic device discussed in the preceding example is demonstrated in two preferred applications. The first application demonstrates the integration of sample processing with chemical separations using the device design depicted in FIG. 8. Two droplets, each containing one dye (rhodamine 123 or fluorescein) were dispensed from reservoirs, merged, mixed, and then delivered to the network of microchannels; from this mixture, a plug was injected and separated, to generate the electropherogram shown in FIG. 15. The results clearly demonstrate excellent separation of the two fluorescent species.

The second application involves the integration of sample processing with mass spectrometry using the device design depicted in FIG. 6. The interface for the MS device is quite similar to the separation device discussed above. The droplet is merged with the interface well following pre-processing, however, in this case, the fluid driving force is different then the preceding example. The hydrostatic pressure of the droplet in the well is used to drive fluid flow through the channel to a nano-electrospray ionization (nESI) tip. An electric field is applied between a Pt electrode inserted into the droplet and the MS orifice, which generates the spray.

Figure 16:
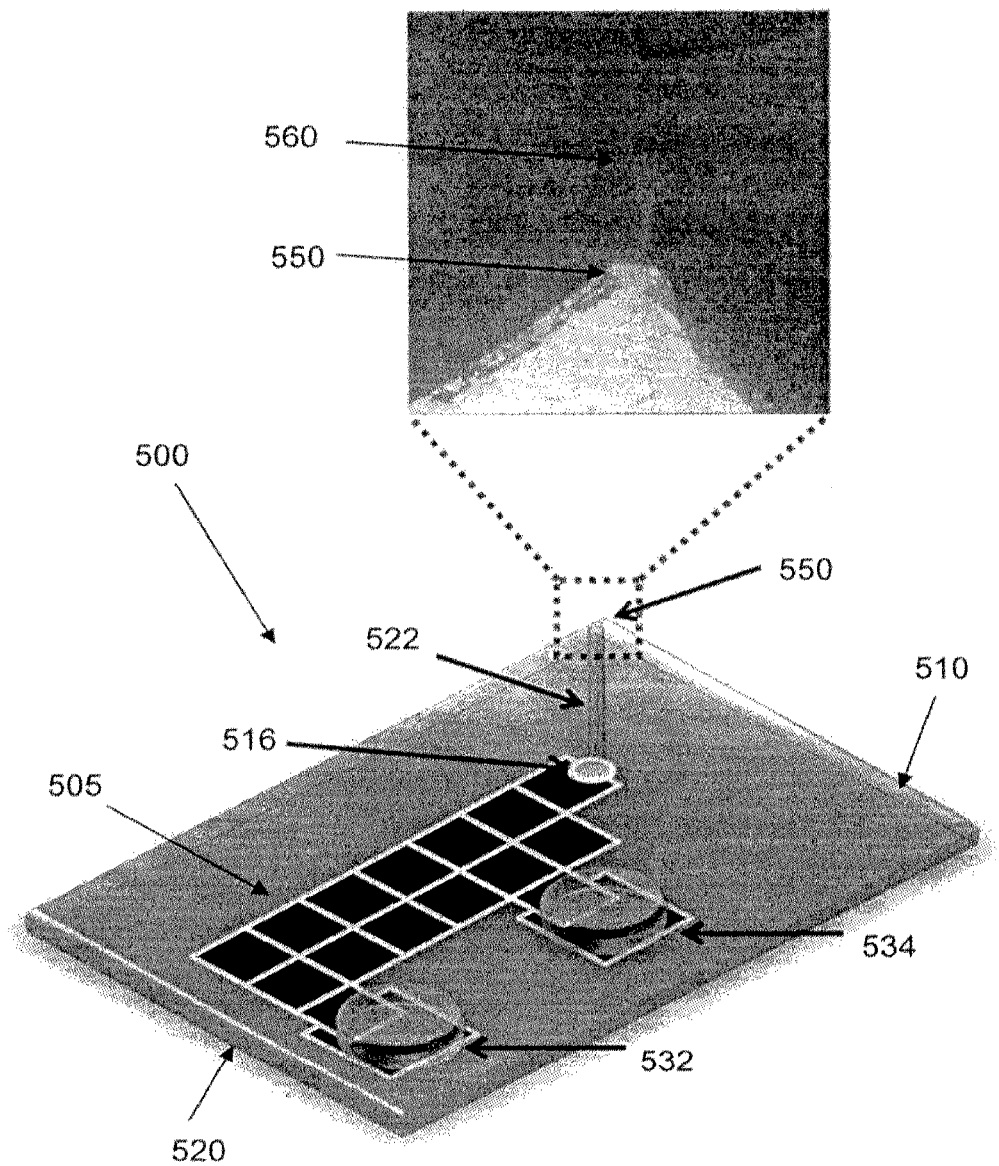
FIG. 16 shows an embodiment of the invention in which a vertical hybrid digital and channel microfluidic device is adapted to provide electrospray for input to a mass spectrometer.

FIG. 16 shows an illustration of such a device, where an embodiment similar to that shown in FIG. 6 is shown. The hybrid device 500 includes a first substrate 510 having a digital microfluidic array 505 overtop of a second substrate 520 that has a single microfluidic channel 522 formed within its top surface. The array 505 includes two reservoir electrodes 532 and 534 for introducing samples and/or reagents onto the array. A well 516 is provided in the first substrate that extends through the substrate and is positioned adjacent to an electrode in array 515. Accordingly, droplets may be transported to well 516, where they are drawn into the well by hydrophilic capillary forces. Well 516 is also positioned above distal end of channel 522, so that droplets transported to well 516 contact an opening of channel 522 and flow into channel 522 under hydrostatic forces. Channel 522 terminates in an external opening located at a corner tip 550 of device 500.

To function as a device for generating electrospray for use in mass spectrometry applications, an electric field is applied between the mass spectrometer orifice and an electrode positioned at tip 550. Applying a sufficient electric field generates an electrospray cone, shown as cone 560 in the inset to FIG. 16.

Figure 17:
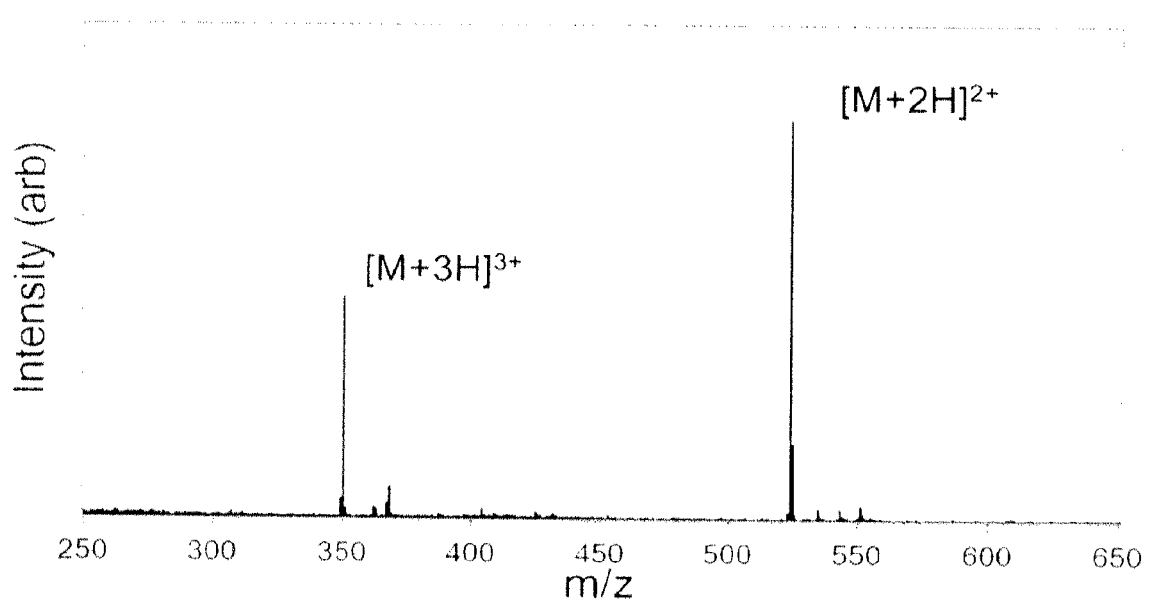
FIG. 17 shows nESI-MS spectrum generated by actuating a droplet containing Angiotensin II (MW 1048) on a vertical hybrid device (similar to that shown in FIG. 16) and then delivering it to a network of microchannels. In this mode, the electrospray is generated by applying high voltage to a platinum wire in contact with the droplet in the access well. As shown, the [M+2H]2+ and [M+3H]3+ peaks of Angiotensin II are observed.

To demonstrate this application, droplets containing a model peptide, angiotensin II, were actuated by DMF, delivered to a microchannel, and then interfaced to nESI-MS by means of methods we reported previously. A representative mass spectrum is shown in FIG. 17. These data confirm that the new method is useful for integrating on-chip sample handling with separations and detection by mass spectrometry. Those skilled in the art will appreciate that the new interface will be useful for myriad applications that would benefit from combining sample processing by digital microfluidics with microfluidic channel separations and detection by mass spectrometry in microchannels (for example, by combining several of the preceding embodiments).

As used herein, the terms, "comprises" and "comprising" are to be construed as being inclusive and open ended, and not exclusive. Specifically, when used in this specification including claims, the terms, "comprises" and "comprising" and variations thereof mean the specified features, steps or components are included. These terms are not to be interpreted to exclude the presence of other features, steps or components.

As used herein, the terms "about" and "approximately, when used in conjunction with ranges of dimensions of particles, compositions of mixtures or other physical properties or characteristics, is meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present invention.

As used herein, the coordinating conjunction "and/or" is meant to be a selection between a logical disjunction and a logical conjunction of the adjacent words, phrases, or clauses. Specifically, the phrase "X and/or Y" is meant to be interpreted as "one or both of X and Y" wherein X and Y are any word, phrase, or clause.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

REFERENCES

1. Jacobson, S. C.; Hergenroder, R.; Koutny, L. B.; Ramsey, J. M., High-Speed Separations on a Microchip, *Anal. Chem.* 1994, 66, 1114-1118.
2. Wu, D.; Qin, J.; Lin, B., Electrophoretic separations on microfluidic chips, *J. Chromatogr. A* 2008, 1184, 542-559.
3. Gottschlich, N.; Culbertson, C. T.; McKnight, T. E.; Jacobson, S. C.; Ramsey, J. M., Integrated microchip-device for the digestion, separation and postcolumn labeling of proteins and peptides, *J. Chromatogr. B* 2000, 745, 243-249.
4. Brivio, M.; Fokkens, R. H.; Verboom, W.; Reinhoudt, D. N.; Tas, N. R.; Goedbloed, M.; Van den Berg, A., Integrated microfluidic system enabling (bio)chemical reactions with on-line MALDI-TOF mass spectrometry, *Anal. Chem.* 2002, 74, 3972-3976.
5. Jacobson, S. C.; Hergenroder, R.; Moore, A. W., Jr.; Ramsey, J. M., Precolumn Reactions with Electrophoretic Analysis Integrated on a Microchip, *Anal. Chem.* 1994, 66, 4127-4132.
6. Ro, K. W.; Lim, K.; Kim, H.; Hahn, J. H., Poly(dimethylsiloxane) microchip for precolumn reaction and micellar electrokinetic chromatography of biogenic amines, *Electrophoresis* 2002, 23, 1129-1137.
7. Washburn, M. P.; Wolters, D.; Yates III, J. R., Large-scale analysis of the yeast proteome by multidimensional protein identification technology, *Nat. Biotechnol.* 2001, 19, 242-247.
8. From Washburn et al.: (1) lyse cells and wash, (2) acidify and digest by cyanogen bromide (overnight), (3) denature in urea, (4) reduce in dithiothreitol, (5) alkylate in iodoacetamide, (6) dilute and digest by Lys-C (overnight), (7) dilute and digest by trypsin (overnight), and (8) purify and concentrate by solid phase extraction.
9. Crabtree, H. J.; Cheong, E. C. S.; Tilroe, D. A.; Backhouse, C. J., Microchip injection and separation anomalies due to pressure effects, *Anal. Chem.* 2001, 73, 4079-4086.
10. Sinton, D.; Li, D., Electroosmotic velocity profiles in microchannels, *Colloids Surf., A* 2003, 222, 273-283.
11. Walker, G. M.; Beebe, D. J., A passive pumping method for microfluidic devices, *Lab Chip* 2002, 2, 131-134.
12. Unger, M. A.; Chou, H. P.; Thorsen, T.; Scherer, A.; Quake, S. R., Monolithic microfabricated valves and pumps by multilayer soft lithography, *Science* 2000, 288, 113-116.
13. Roman, G. T.; Kennedy, R. T., Fully integrated microfluidic separations systems for biochemical analysis, *J. Chromatogr. A* 2007, 1168, 170-188.
14. Teh, S.-Y.; Lin, R.; Hung, L.-H.; Lee, A. P., Droplet microfluidics, *Lab Chip* 2008, 8, 198-220.
15. Edgar, J. S.; Pabbati, C. P.; Lorenz, R. M.; He, M.; Fiorini, G. S.; Chiu, D. T., Capillary electrophoresis separation in the presence of an immiscible boundary for droplet analysis, *Anal. Chem.* 2006, 78, 6948-6954.
16. Roman, G. T.; Wang, M.; Sandlin, Z.; Jennings, C.; Schultz, K.; Kennedy, R. T., Sampling and Electrophoretic Analysis of Segmented Flow Streams in a Microfluidic Device, Anal. Chem. 2008, DOI: 10.1021/ac801317t.
17. Wheeler, A. R. Science 2008, 322, 539-540.
18. Pollack, M. G.; Fair, R. B.; Shenderov, A. D. Applied Physics Letters 2000, 77, 1725-1726.
19. Lee, J.; Moon, H.; Fowler, J.; Schoellhammer, T.; Kim, C.-J. Sensors & Actuators A 2002, 95, 259-268.
20. Luk, V. N.; Mo, G. C.; Wheeler, A. R. Langmuir 2008, 24, 6382-6389.
21. Chatterjee, D.; Hetayothin, B.; Wheeler, A. R.; King, D. J.; Garrell, R. L. Lab on a Chip 2006, 6, 199-206.
22. Brassard, D.; Malic, L.; Normandin, F.; Tabrizian, M.; Veres, T. Lab on a Chip 2008, 8, 1342-1349.
23. Cho, S. K.; Moon, H.; Kim, C.-J. Journal of Microelectromechanical Systems 2003, 12, 70-80.
24. Luk, V. N.; Wheeler, A. R. Analytical Chemistry 2009, 81, 4524-4530.
25. Jebrail, M. J.; Wheeler, A. R. Analytical Chemistry 2009, 81, 330-335.
26. Fair, R. B.; Digital microfluidics: is a true lab-on-a-chip possible? Microfluid Nanofluid 2007, 3, 245-281.

Therefore what is claimed is:

1. A hybrid microfluidic device comprising:
   a first substrate comprising first and second opposing surfaces, wherein a portion of said first surface has a digital microfluidic array formed thereon;
   a second substrate comprising a third surface, said second substrate comprising an elongate microfluidic channel formed proximal to said third surface, said elongate microfluidic channel extending to a side surface of said second substrate to define an opening;
   wherein said third surface is attached to said first surface without contacting said digital microfluidic array, such that said opening is located adjacent to an array element of said digital microfluidic array, and such that said elongate microfluidic channel is absent of microfluidic electrodes;
   wherein said digital microfluidic array is capable of transporting a fluidic droplet to said array element for contacting the droplet with said opening of said elongate microfluidic channel; and
   wherein said elongate microfluidic channel comprises a cross-sectional size that is sufficiently small to promote injection of the droplet from the array element into the elongate microfluidic channel via capillary forces.

2. The hybrid microfluidic device according to claim 1 further comprising a fluidic interfacing means for transferring a droplet contacted with said opening into said elongate microfluidic channel.

3. The hybrid microfluidic device according to claim 2 wherein said fluidic interfacing means comprises capillary action.

4. The hybrid microfluidic device according to claim 2 wherein said elongate microfluidic channel is pre-filled with a liquid and said fluidic interfacing means comprises a Laplace pressure from a surface of the droplet.

5. The hybrid microfluidic device according to claim 2 wherein said device further comprises a first electrode located in fluid communication with a liquid within said elongate microfluidic channel and a second electrode in contact with the droplet, and wherein said fluidic interfacing means comprises electrokinetic injection obtained by applying a voltage between said first and second electrodes.

6. The hybrid microfluidic device according to claim 2 wherein said opening is a first opening, and wherein said elongate microfluidic channel comprises a second opening accessible from a location external to said device, and wherein said fluidic interfacing means comprises a pump means connected to said second opening.

7. The hybrid microfluidic device according to claim 1 wherein said opening is a first opening, and wherein said microfluidic channel further comprises a second opening, and wherein said device further comprises an electrode for electrically contacting a fluid within said elongate microfluidic channel.

8. The hybrid microfluidic device according to claim 7 wherein said second opening comprises an electrospray aperture.

9. The hybrid microfluidic device according to claim 7 wherein said second opening is provided at a corner of said second substrate.

10. The hybrid microfluidic device according to claim 7 wherein said electrode is provided in said first opening to electrically contact a fluid contained within said elongate microfluidic channel.

11. A system for providing performing mass analysis, said system comprising:
a hybrid microfluidic device according to claim 8;
a mass analysis device; and
a means for applying a potential difference between said electrode and an inlet of said mass analysis device.

12. The hybrid microfluidic device according to claim 1 wherein said elongate microfluidic channel is formed as an open channel within said third surface of said second substrate, such that said elongate microfluidic channel is enclosed along a length thereof by the attachment of the second substrate to the first substrate.

13. The hybrid microfluidic device according to claim 1 wherein said elongate microfluidic channel comprises a solid phase material for performing one of solid phase separation and solid phase extraction.

14. The hybrid microfluidic device according to claim 1 wherein said second substrate comprises a network of microfluidic channels, said network of microfluidic channels comprising said elongate microfluidic channel.

15. The hybrid microfluidic device according to claim 14 wherein said elongate microfluidic channel is a first elongate microfluidic channel, and wherein said network of microfluidic channels comprises a second elongate microfluidic channel intersecting said first elongate microfluidic channel for performing electrokinetic pinched injection into said second microfluidic channel and for performing one of electrophoretic and electrochromatographic separation within said second microfluidic channel.

16. A hybrid microfluidic device comprising:
a first substrate comprising first and second opposing surfaces, wherein said first surface has a digital microfluidic array formed thereon;
said first substrate having a hydrophilic access port formed therein, said hydrophilic access port extending from said first surface to said second surface, wherein said hydrophilic access port is positioned adjacent to an array element of said digital microfluidic array to promote the flow of a droplet from said array element through said hydrophilic access port;
a second substrate comprising a third surface, wherein an elongate microfluidic channel is formed within said second substrate within a microfluidic plane that is parallel to said third surface;
wherein said third surface is attached to said second surface such that said access port is in fluid communication with said elongate microfluidic channel through an opening in said third surface, and such said microfluidic plane is parallel to said digital microfluidic array;
wherein said digital microfluidic array is capable of transporting a droplet to said array element for contacting the droplet with said hydrophilic access port; and
wherein said elongate microfluidic channel comprises a cross-sectional size that is sufficiently small to promote injection of the droplet from the hydrophilic access port into the elongate microfluidic channel via capillary forces.

17. The hybrid microfluidic device according to claim 16 wherein said elongate microfluidic channel is formed as an open channel within said third surface of said second substrate, such that said elongate microfluidic channel is enclosed along a length thereof by the attachment of the second substrate to the first substrate.

18. The hybrid microfluidic device according to claim 16 wherein said opening is a first opening, and wherein said channel comprises a second opening accessible from a location external to said device.

19. The hybrid microfluidic device according to claim 18 wherein said second opening comprises an electrospray aperture.

20. The hybrid microfluidic device according to claim 19 wherein said second opening is provided at a corner of said second substrate.

21. The hybrid microfluidic device according to claim 16 wherein said device further comprises a first electrode located in fluid communication with a liquid within said elongate microfluidic channel and a second electrode in contact with the droplet for performing electrokinetic injection.

22. The hybrid microfluidic device according to claim 16 wherein said digital microfluidic array further comprises a dielectric spacer layer and an additional substrate affixed thereon, wherein a planar channel is formed between said first surface of said first substrate and an additional surface of said additional substrate.

23. The hybrid microfluidic device according to claim 16 wherein said elongate microfluidic channel comprises a solid phase material for performing one of solid phase separation and solid phase extraction.

24. The hybrid microfluidic device according to claim 16 wherein said second substrate comprises a network of microfluidic channels, said network of microfluidic channels comprising said elongate microfluidic channel.

25. The hybrid microfluidic device according to claim 24 wherein said elongate microfluidic channel is a first elongate microfluidic channel, and wherein said network of microfluidic channels comprises a second elongate microfluidic channel intersecting said first elongate microfluidic channel for performing electrokinetic pinched injection into said second microfluidic channel and for performing one of electrophoretic and electrochromatographic separation within said second microfluidic channel.

* * * * *